(12) United States Patent
Abrignani

(10) Patent No.: US 6,777,538 B2
(45) Date of Patent: *Aug. 17, 2004

(54) BINDING PROTEIN

(75) Inventor: Sergio Abrignani, Castelnuovo Berardenga (IT)

(73) Assignee: Chiron S.r.l., Siena (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/755,251

(22) Filed: Jan. 5, 2001

(65) Prior Publication Data

US 2001/0027565 A1 Oct. 4, 2001

Related U.S. Application Data

(63) Continuation of application No. 09/011,910, filed as application No. PCT/IB96/00943 on Aug. 30, 1996.

(30) Foreign Application Priority Data

Sep. 1, 1995 (GB) .............................. 9517926

(51) Int. Cl.[7] .......................... C07K 14/47; C07K 1/14
(52) U.S. Cl. ...................... 530/350; 530/417; 530/420; 435/5
(58) Field of Search ................................ 530/350, 417, 530/420; 424/277.1; 514/2, 21; 435/5

(56) References Cited

FOREIGN PATENT DOCUMENTS

| EP | 0 318 216 B1 | 5/1989 |
|---|---|---|
| EP | 0 388 232 A1 | 9/1990 |
| EP | 0 565 172 | 10/1993 |
| WO | WO 93/04205 | 3/1993 |
| WO | WO 96/04376 | 2/1996 |
| WO | WO 96/05513 | 2/1996 |

OTHER PUBLICATIONS

Levy et al., Structure and Membrane Topology of TAPA–1, The Journal of Biological Chemistry 266(22):14597–14602, 1991.*
Pileri et al., Binding of Hepatitis C Virus to CD81, Science 282:938–941, 1988.*
Chien, et al., "Diagnosis of hepatitis C virus (HCV) infection using an immunodominant chimeric polyprotein to capture circulating antibodies: Reevaluation of the role of HCV in liver disease," *Proc. Natl. Acad. Sci. USA*, 1992, 89, 10011–10015.
Choo, Q.L., et al., "Genetic organization and diversity of the hepatitis C virus," *Proc. Natl. Acad. Sci. USA*, 1991, 88, 2451–2455.
Gething, M.J., et al., "Construction of influenza haemagglutinin genes that code for intracellular and secreted forms of the protein," *Nature*, 1992, 300, 598–603.
Laemmli, U.K., "Cleavage of structural proteins during the assembly of the head of bacteriophage T4," *Nature*, 1970, 227, 680–685.
Levy, S. et al., "CD81 (TAPA–1): A Molecule Involved in Signal Transduction and Cell Adhesion in the Immune System," *Annu. Rev. Immunol.*, 1998, 16, 89–109.
Minutello, et al., "T–Cell response of HCV imperipheral blood and liver and its coloration with protection and pathogenicity," *J. Hepatology*, 1992, 17(suppl. 1), 55–56.
Morré, D.J., et al., "[43] Plasma and internal membranes from cultured mammalian cells," *Methods in Enzymology*, 1994, 228, 448–450.
Rice, C.M., *Hepatology*, 1999, 29(3), 990–992.
Rosa, D., et al., "A quantitative test to estimate neutralizing antibodies to the hepatitis C virus: Cytofluorimetric assessment of envelope glyocprotein 2 binding to target cells," *Proc. Natl. Acad. Sci. USA*, 1996, 93, 1759–1763.
Rowlands, et al., " Cells of the immune system," in Henry, J.B.(Ed.), *Clinical Diagnosis & Management by Laboratory Methods*, 18th Ed., 1991, W.B. Saunders Company, Philadelphia.
Shimonaka, et al., "Purification and biological characterization of epitaxin, a fibroblast–derived motility factor for epithelial cells," *J. Biological Chemistry*, 1994, 269(19), 14284–14289.
Spaete, R.R., et al., "Characterization of the hepatitis C virus E2/NS1 gene product expressed in mammalian cells," *Virology*, 1992, 188, 819–830.
Lambot et al. (2002), "Reconstitution of Hepatitis C Virus Envelope Glycoproteins into Liposomes as a Surrogate Model to Study Virus Attachment," *J of Biol Chem* 277(23):20625–20630.
Petracca et al. (2000), "Structure–Function Analysis of Hepatitus C Virus Envelope–CD81 Binding," *J of Virol* 74(10):4824–4830.
Pileri et al. (1999), "Is CD81 the Key to Hepatitis C Virus Entry," *Hepatology Elsewhere* 29(3):990–992.

* cited by examiner

*Primary Examiner*—Donna C. Wortman
(74) *Attorney, Agent, or Firm*—Roberta L. Robins; Alisa A. Harbin; Robert P. Blackburn

(57) ABSTRACT

A 24 kd protein capable of binding the E2 envelope protein of hepatitis C virus (HCV), and functionally equivalent variants or fragments of the 24 kd protein, are disclosed. Processes for production and purification of the 24 kd protein, and functionally equivalent variants or fragments thereof, are also disclosed.

10 Claims, 14 Drawing Sheets

MOLT 4

JURKAT

K562

EBV-B

ADENOCARCINOMA

HUH 7

PURIFIED RA

PURIFIED RO

KC3 TCC

SAG S9 TCC

BINDING PROTEIN

This Application: is a continuation of application Ser. No. 09/011,910, filed: Feb. 17, 1998, which is a National Stage regular U.S. Application claiming priority of PCT/IB96/00943, filed, Aug. 30, 1996, which claims priority of GBRI 9517926.3, filed, Sep. 1, 1995, all applications, incorporated by reference in their entireties. This application claims benefit of International Application No. PCT/IB96/00943; filed on Aug. 30, 1996, which was published under PCT Article 21(2) in English."

FIELD OF THE INVENTION

The present invention relates to proteins capable of binding the E2 envelope protein of hepatitis C virus (HCV) and to processes for production and purification.

The invention also relates to the use of the proteins in therapy and diagnosis and to pharmaceutical compositions and diagnostic kits for such uses. The invention also relates to a process for screening putative molecules for competition with HCV for receptor binding. The invention also relates to an animal model for HCV infection.

BRIEF DESCRIPTION OF THE PRIOR ART

HCV (previously known as Non-A Non-B hepatitis—NANBV)is a positive sense RNA virus of about 10000 nucleotides with a single open reading frame encoding a polyprotein of about 3000 amino acids. Although the structure of the virus has been elucidated by recombinant DNA techniques (1, 2), the virus itself has not been isolated and the functions of the various viral proteins produced by proteolysis of the polyprotein have only been inferred by analogy with other similar viruses of similar genomic organisation (3).

The viral proteins are all available in recombinant form, expressed in a variety of cells and cell types, including yeast, bacteria, insect and mammalian cells (4,5).

Two proteins, named E1 and E2 (corresponding to amino acids 192–383 and 384–750 respectively) have been suggested to be external proteins of the viral envelope which are responsible for the binding of virus to target cells (3).

HCV research is hindered very considerably by the limited host range of the virus. The only reliable animal model for HCV infection is the chimpanzee and it is not possible to propagate HCV in tissue culture.

In our copending International patent application PCT/IB95/00692, we describe a method employing flow cytometry to identify cells carrying the HCV receptor. We have shown that, by labelling cells with recombinant E2 envelope protein, it is possible to sort cells using flow cytometry, isolating those cells capable of specific binding to the E2 and therefore potentially carrying the HCV receptor. Employing this technique, we have identified a protein capable of binding to the E2 envelope protein of HCV which we believe to be the receptor for HCV, thereby enabling overcoming many problems in the art.

SUMMARY OF THE INVENTION

According to the present invention, there is provided a protein having a molecular weight of about 24 kD and capable of specifically binding to a protein of hepatitis C virus, or a functionally equivalent variant or fragment thereof.

It will be understood by the skilled person that molecular weights measured as described below using electrophoresis are inherently subject to interpretation since they are measured relative to standard molecular weight markers. However, in the context of this specification the expression "24 kd" is unambiguous when read in context, since only one such protein is obtained by following the processes described below with the defined characteristic of binding to hepatitis C virus.

A significant characterising feature of the protein according to the present invention is its ability to bind specifically to an HCV protein, preferably an envelope protein, particularly the E2 protein.

On the basis of this specificity and other features described below, we infer that the 24 kd protein of the invention is a cellular receptor for HCV.

We have shown that the protein is ubiquitous in humans amongst the cell types we have tested, paralleling the situation found for many other viruses of this type (such as vaccinia virus and influenza virus).

We have shown that the protein is species specific in a manner which matches the species specificity of HCV itself.

Our experiments have shown that the 24 kd protein is functionally unglycosylated. Treatment with glycosidases does not affect the ability of the 24 kd protein to bind to the E2 protein and does not appear significantly to reduce the molecular weight. We infer therefore that, if the protein is glycosylated at all, glycosylation must be restricted to a small number of sugar moieties and is not necessary for functional activity of the protein.

Our experiments have also shown that the protein is a transmembrane protein, again suggesting that it is a cellular receptor.

Finally, experiments with cell lines hyperexpressing the protein indicate that such cells are prone to aggregation suggesting that the protein may be an adhesion molecule of some form.

The 24 kd protein may be in its naturally occurring form, albeit isolated from its native environment, or may be modified, provided that it retains the functional characteristic of at least binding to the E2 protein of HCV. For example, the 24 kd protein may be modified chemically to introduce one or more chemical modifications to the amino acid structure. It may include modifications of the amino acid sequence involving one or more insertions, deletions or replaced amino acids. It may, for example, be truncated by the removal of a functional part of the transmembrane domain to facilitate ready production by recombinant DNA means in a suitable mammalian host cell (6).

The protein of the present invention may be purified from cells exhibiting binding to an HCV protein, such as the E2 protein.

According to the present invention there is provided a process for the preparation of a protein according to the invention or a functionally equivalent variant or fragment thereof comprising the step of culturing cells exhibiting binding to an HCV protein and purifying from a cell preparation a protein according to the invention.

The cells may be transformed or untransformed mammalian cells and are suitably human cells.

The cells may be screened for binding to an HCV protein using fluorescence flow cytometry or any other suitable assay. For example, the present description provides the information necessary to produce the 24 kd protein or a functionally equivalent variant or fragment thereof which then itself be used to assay for further cells carrying the protein.

The cell preparation may be a cell membrane preparation but is preferably a plasma cell membrane preparation.

Preferably the cells are selected and cloned to provide hyperexpression of the protein of the present invention.

We have discovered that the protein is precipitated by ammonium sulphate at between 33 and 50% of saturation.

Preferably, therefore, the cell preparation is subjected to an ammonium sulphate precipitation purification step employing ammonium sulphate at between 33 and 50%. Suitably a first precipitation is conducted at less than 33% and precipitated material discarded followed by precipitation of the desired material at between 33 and 50%, most preferably 50%.

Preferably, the purification involves at least one step of hydrophobic interaction chromatography.

We have also discovered that the protein is stable to acetone precipitation, thereby providing a still further characterisation and a useful purification process step.

Most preferably in optimised form, the process of purification comprises the steps of:
  i) preparing a plasma cell membrane preparation of mammalian cells selected for hyperexpression of the 24 kd protein of the invention,
  ii) subjecting the preparation to ammonium sulphate precipitation at less than 33% saturation and retaining the supernatant,
  iii) subjecting the supernatant to ammonium sulphate precipitation at between 33 and 50% saturation and retaining the precipitate, and
  iv) resuspending the precipitate and subjecting it to hydrophobic interaction chromatography As an alternative to purification from wild-type cell lines, the protein of the invention or a functionally equivalent variant or fragment thereof may be made by any suitable synthetic process including chemical synthesis. Suitably, the protein or a functionally equivalent variant or fragment thereof is made by expression of a gene encoding the protein in a suitable host cell or animal.

According to a further aspect of the invention, there is provided a method for treating an infection of HCV comprising administering to a patient an amount of the protein of the invention or a functionally equivalent variant or fragment thereof effective to reduce the infectivity of the virus.

Since the infection mechanism of HCV appears to depend, in part, upon the availability of a cell surface receptor, making available a soluble form of the protein of the invention will act as an antagonist of binding of HCV to the cellular receptor thus reducing or preventing the infection process and thereby treating the disease.

A suitable form of the protein of the invention might comprise, for example, a truncated form of the protein from which the transmembrane domain has been removed either by a protein cleavage step or, by design, in a chemical or recombinant DNA synthesis.

Alternatively, a hybrid particle comprising at least one particle-forming protein, such as hepatitis B surface antigen or a particle-forming fragment thereof, in combination with the protein of the invention or a functionally equivalent variant or fragment thereof could be used as an antagonist of binding of HCV to the cellular receptor.

According to a further aspect of the invention, there is provided a pharmaceutical composition comprising a protein of the invention or a functionally equivalent variant or fragment thereof, optionally as a pharmaceutically acceptable salt, in combination with a pharmaceutically acceptable carrier.

The pharmaceutical composition may be in any appropriate form for administration including oral and parenteral compositions.

A process is also provided for making the pharmaceutical composition, in which a protein of the present invention or a functionally equivalent variant or fragment thereof is brought into association with a pharmaceutically acceptable carrier.

According to a further aspect of the invention, there is provided a protein of the invention or a functionally equivalent variant or fragment thereof for use as a pharmaceutical.

According to a further aspect of the invention, there is provided the use of a protein of the invention or a functionally equivalent variant or fragment thereof in the manufacture of a medicament for the treatment of an HCV infection.

The ability of a protein of the invention or a functionally equivalent variant or fragment thereof to bind to HCV permits the use of the protein or a functionally equivalent variant or fragment thereof as a diagnostic for HCV infection, for example in an ELISA or RIA.

A soluble form of the protein could, for example, be used in an ELISA form of assay to measure neutralising antibodies in serum.

According to a further aspect of the invention, there is provided an assay for HCV antibodies in a serum sample comprising the step of allowing competitive binding between antibodies in the sample and a known amount of an HCV protein for binding to a protein of the invention or a functionally equivalent variant or fragment thereof and measuring the amount of the known HCV protein bound.

Preferably, the protein of the invention or functionally equivalent variant or fragment thereof is immobilised in a solid support and the HCV protein, which may suitably be E2 HCV envelope protein, optionally recombinant E2 protein, is labelled, suitably enzyme labelled.

In an assay of this form, competitive binding between antibodies and the HCV protein for binding to the protein of the invention results in the bound HCV protein being a measure of antibodies in the serum sample, most particularly, neutralising antibodies in the serum sample.

A significant advantage of the assay is that measurement is made of neutralising antibodies directly (i.e those which interfere with binding of HCV envelope protein to the cellular receptor). Such an assay, particularly in the form of an ELISA test has considerable applications in the clinical environment and in routine blood screening.

Also, since the assay measures neutralising antibody titre, the assay forms a ready measure of putative vaccine efficacy, neutralising antibody titre being correlated with host protection.

In a further aspect of the invention, there is provided a diagnostic kit comprising the protein of the invention or a functionally equivalent variant or fragment thereof. Preferably the kit also contains at least one HCV labelled HCV protein, optionally enzyme labelled.

The protein of the invention or a functionally equivalent variant or fragment thereof may be used to screen for chemical compounds mimicking the HCV surface structure responsible for binding to the HCV receptor.

According to a further aspect of the invention, there is provided a method for screening chemical compounds for ability to bind to the region of HCV responsible for binding to a host cell, comprising measuring the binding of a chemical compound to be screened to a protein of the invention or a functionally equivalent variant or fragment thereof.

This aspect of the invention encompasses the products of the screening process whether alone, in the form of a pharmaceutically acceptable salt, in combination with one or more other active compounds and/or in combination with one or more pharmaceutically acceptable carriers. Processes for making a pharmaceutical composition are also provided in which a chemical compound identified by the process of the invention is brought into association with a pharmaceutically acceptable carrier.

The chemical compound may be an organic chemical and may contain amino acids or amino acid analogues. Preferably however the chemical compound is a polypeptide or a polypeptide which has been chemically modified to alter its specific properties, such as the affinity of binding to the protein of the invention or a functionally equivalent variant or fragment thereof or its stability in vivo.

At present, the only available animal model is the chimpanzee, which is a protected species. Experiments on such animals pose a number of difficulties which together result in a very considerable expense (a one year experiment with one chimpanzee can cost $70,000). Compared to this, a mouse model would be far more acceptable. Unfortunately, as described below the HCV receptor, whilst ubiquitous in humans and found in chimpanzees, is absent in other mammals. A transgenic mammal, for example a mouse, carrying the HCV receptor on the cell surface would be of great benefit to HCV research and the development of vaccines.

According to a further aspect of the invention, there is provided a transgenic non-human mammal, suitably a mouse, carrying a transgene encoding a protein of the invention or a functionally equivalent variant or fragment thereof.

The transgenic animal of the invention may carry one or more other transgenes to assist in maintaining an HCV infection.

There is also provided a process for producing a transgenic animal comprising the step of introducing a DNA encoding a protein of the invention or a functionally equivalent variant or fragment thereof into the embryo of a non-human mammal, preferably a mouse.

DETAILED DESCRIPTION OF THE INVENTION

Figure 1:
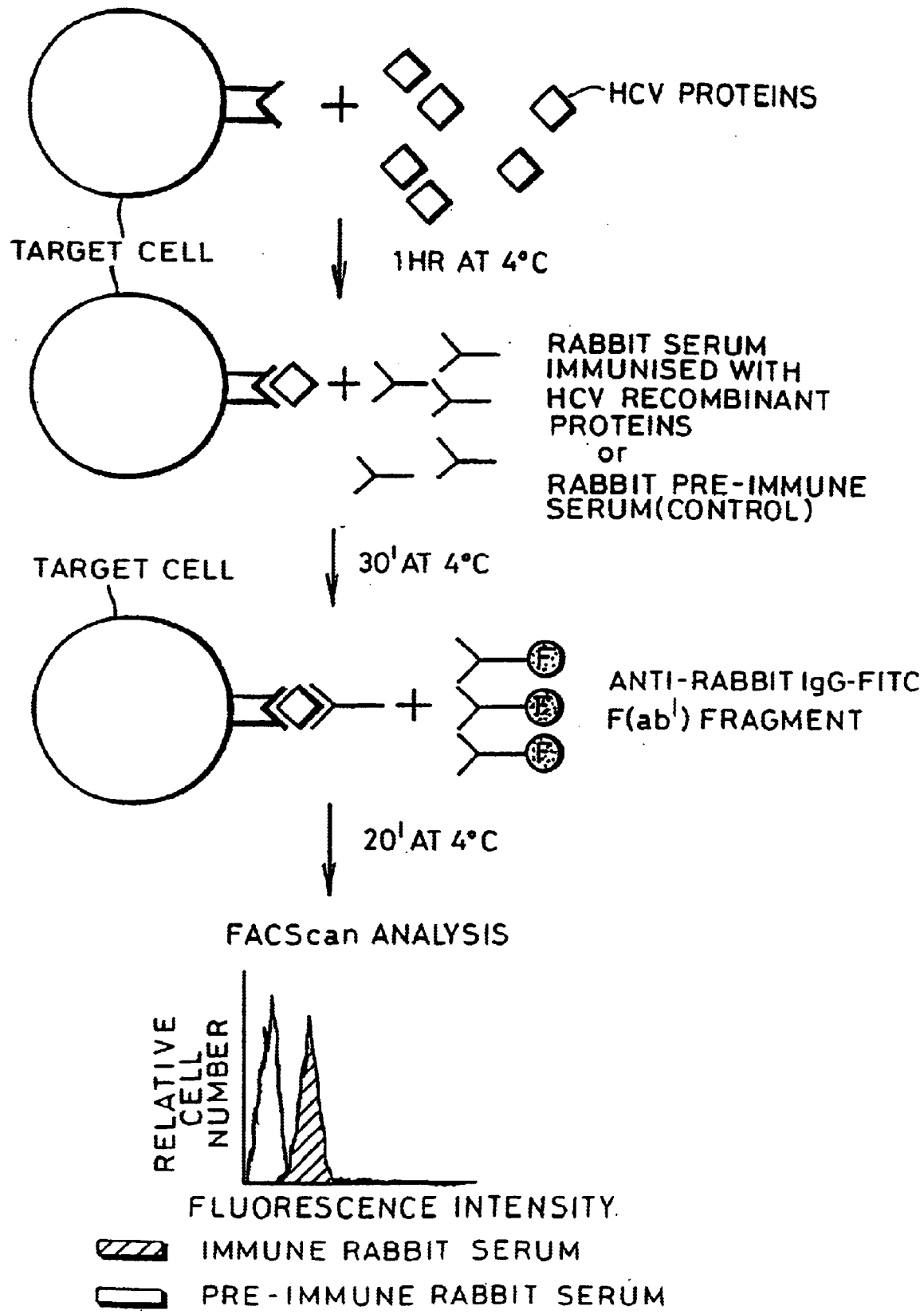
FIG. 1 is a schematic diagram describing an assay in which HCV receptor-binding ligands bind to receptors on HCV receptor target cells and are measured by first binding rabbit anti-HCV antibody and then by binding a labelled anti-rabbit IgG-FITC F(ab') fragment prior to cell separation by FACScan analysis.
Figure 2A:
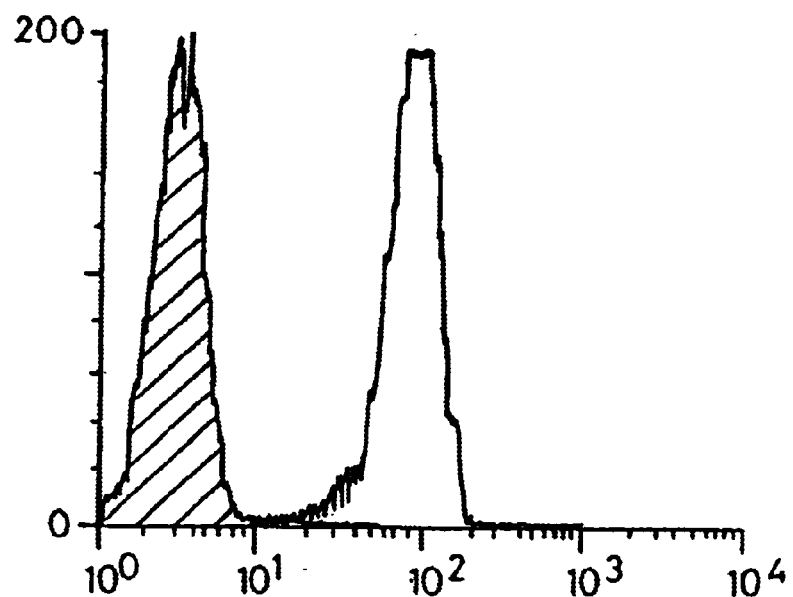
FIG. 2 is a computer-generated histogram depicting the results of a FACScan analysis of binding of HCV protein to haematopoietic cells (MOLT-4, Jurkat, K562, Daudi, EBV-B) and epithelial cells (Hela, Adenocarcinoma and Huh 7) resulting from binding with HCV proteins (filled curve unlabelled control, open curve labelled). The plot is of cell population against fluorescence intensity.
Figure 2B:
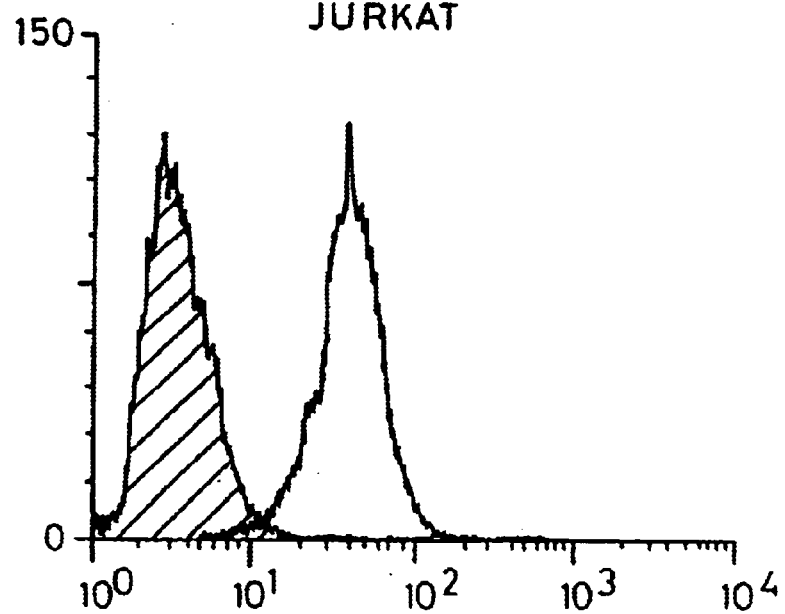
Figure 2C:
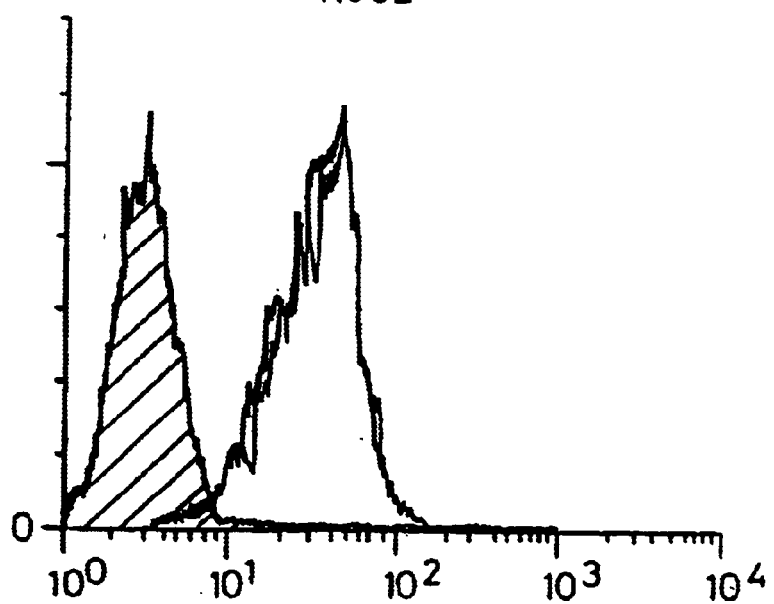
Figure 2D:
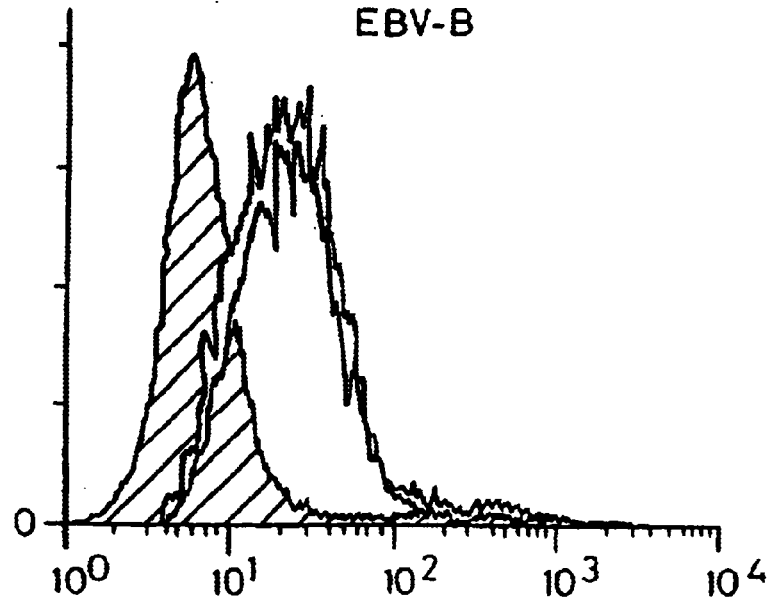
Figure 2E:
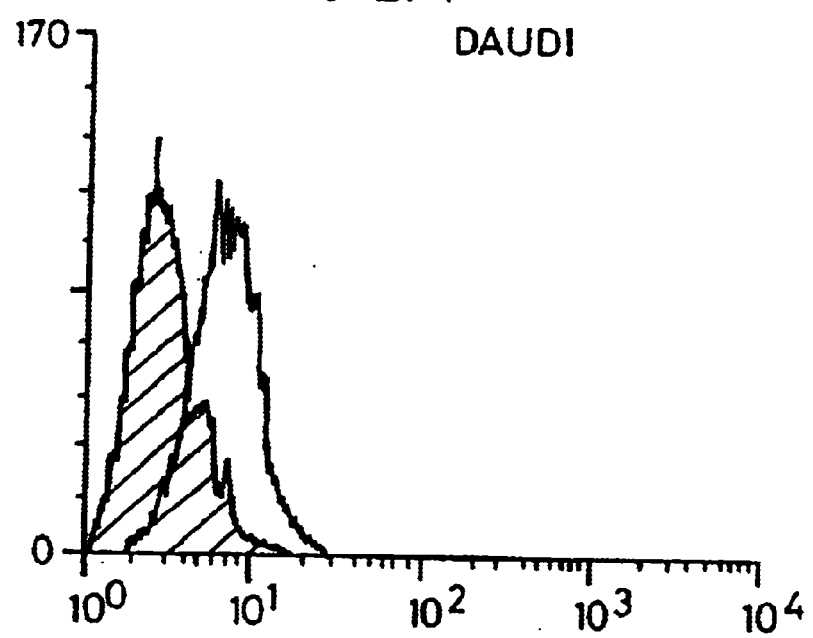
Figure 2F:
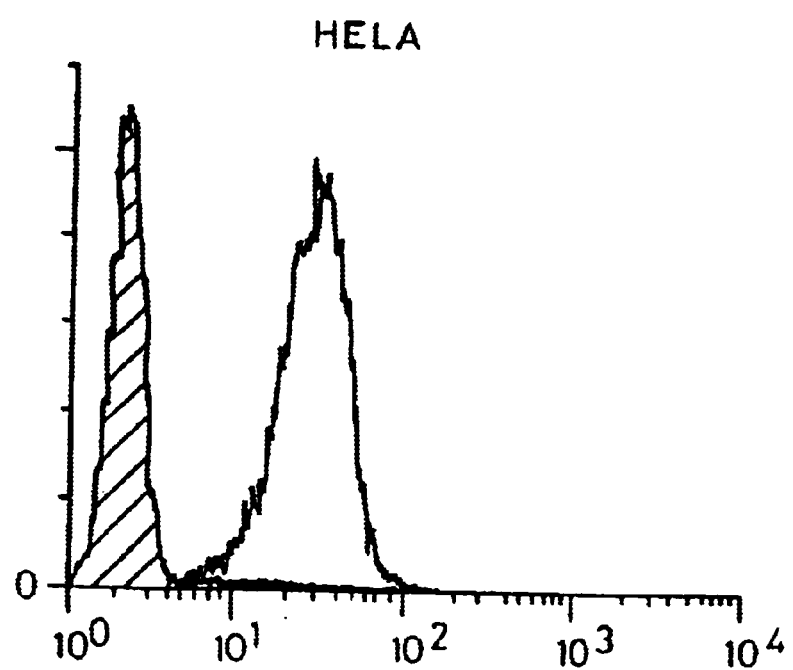
Figure 2G:
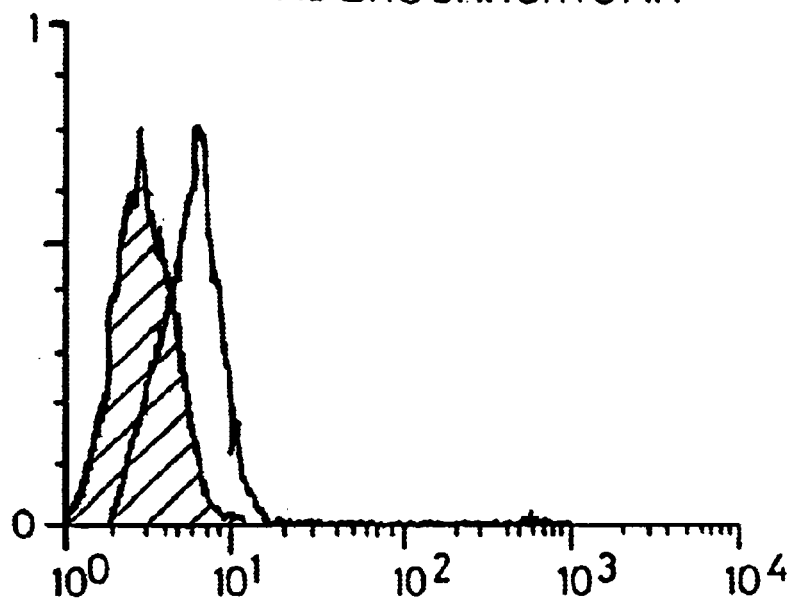
Figure 2H:
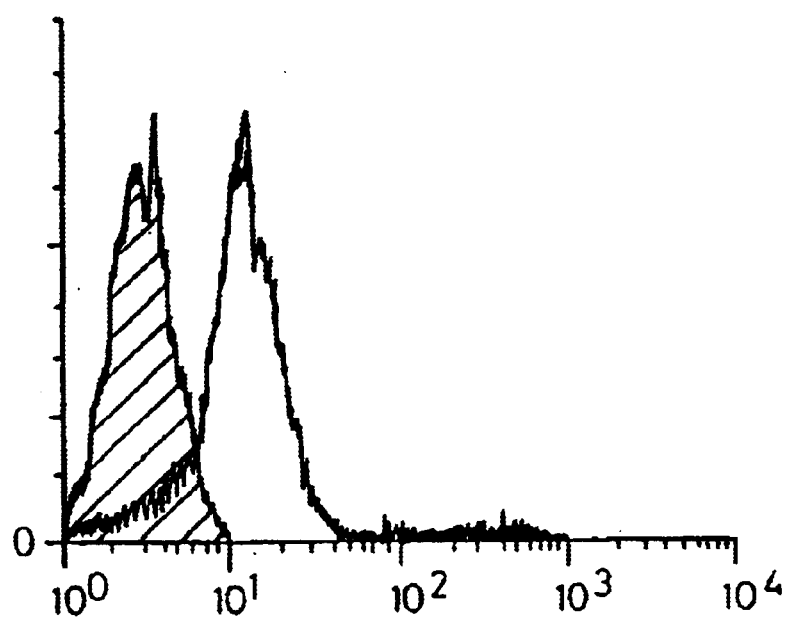
Figure 3A:
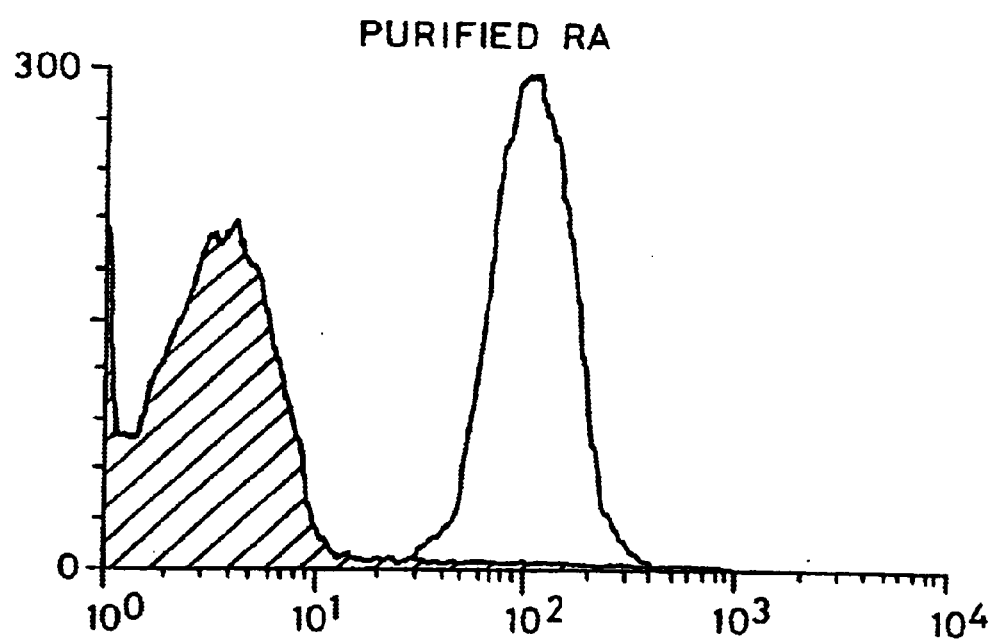
FIG. 3 is a computer-generated histogram depicting the results of a FACScan analysis of purified RA, purified RO, cord blood purif. RA, cord blood RA pha stim., KC3 T-cell clone (TCC) and SAG S9 TCC, which were tested for binding to recombinant HCV E2 protein expressed in CHO cells (filled curve unlabelled control, open curve labelled). The plot is of cell population against fluorescence intensity.
Figure 3B:
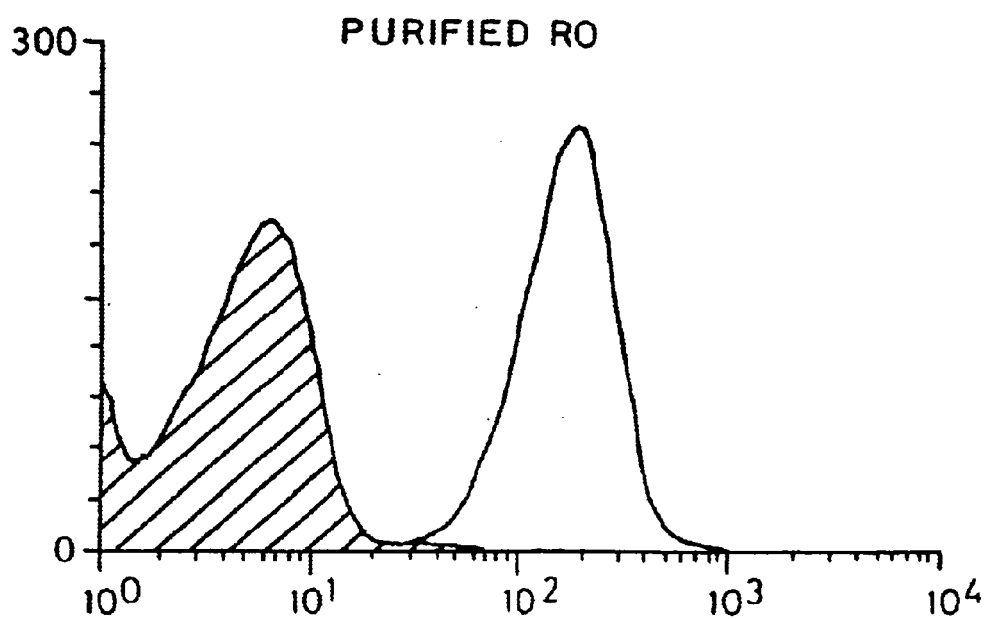
Figure 3C:
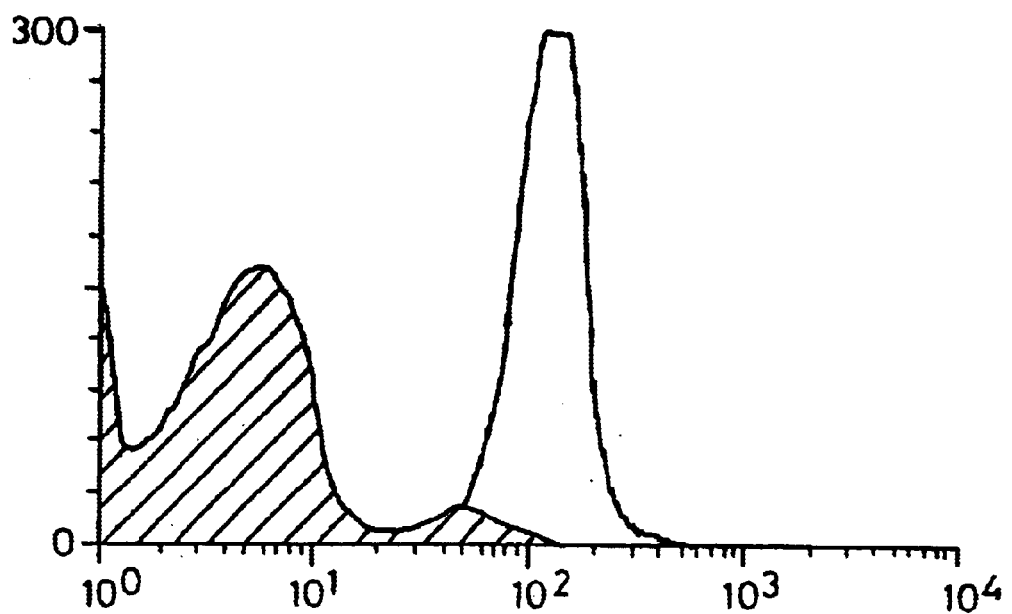
Figure 3D:
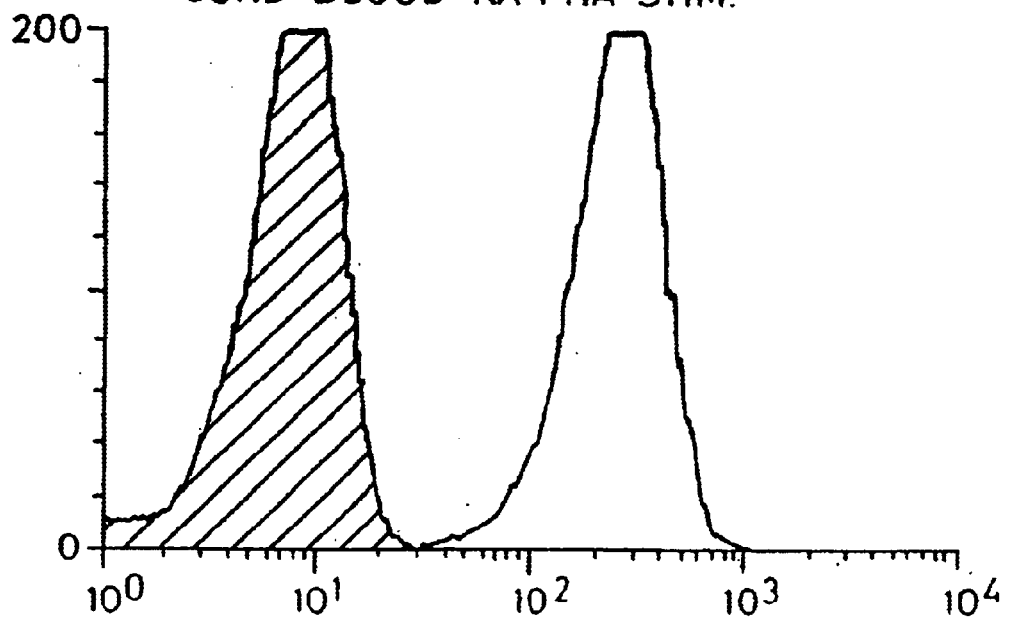
Figure 3E:
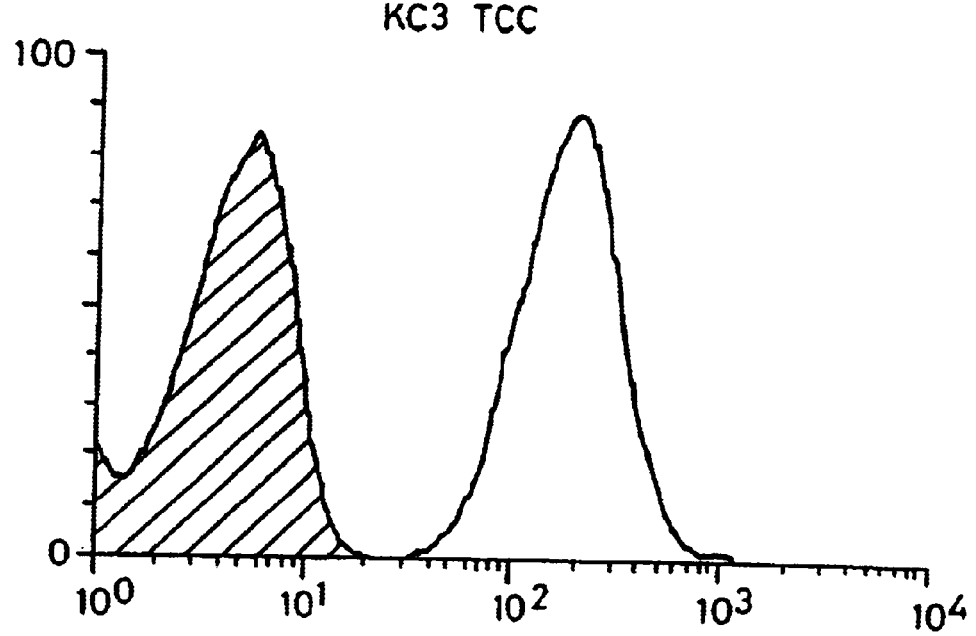
Figure 3F:
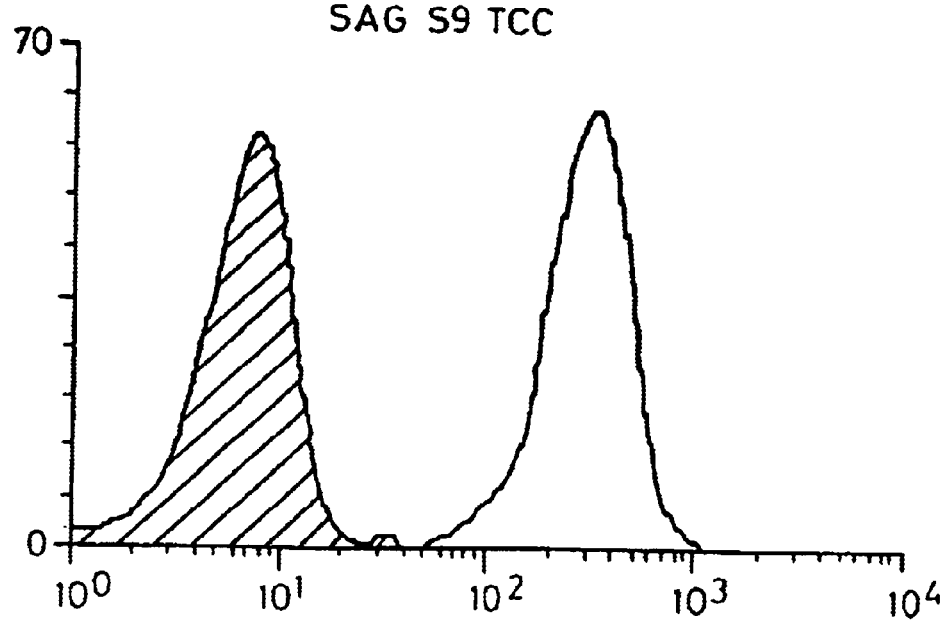

The arrangement of the detailed description is as follows:

| | | |
|---|---|---|
| 1. | General Description | 13 |
| 2. | Cellular Assay | 13 |
| 2.1. | FACS analysis of cells binding to E2 | 13 |
| 2.2. | Effect of E2 modification on binding | 15 |
| | 2.2.1. E2 reduction | 16 |
| | 2.2.2. E2 deglycosylation | 16 |
| 2.3. | Monoclonal antibody production | 17 |
| 3. | Preparation of 24 kd putative receptor | 17 |
| 3.1. | 24 kd protein preparation from MOLT-4 cells | 17 |
| | 3.1.1. Membrane purification | 17 |
| | 3.1.2. Plasma membrane purification | 18 |
| 3.2. | Hyperexpressing MOLT-4 cells | 20 |
| 4. | Characterisation of Receptor | 20 |
| 4.1. | Western blot protocol | 20 |
| | 4.1.1. Membrane proteins | 21 |
| | 4.1.2. Plasma membrane proteins | 22 |
| | 4.1.3. Western blot of PBMC cells | 23 |
| 4.2. | Cell surface expression of receptor | 23 |
| 4.3. | Effect of enzymes on 24 kd protein binding | 24 |
| | 4.3.1. Flow cytometry | 24 |
| | 4.3.2. Western blot on MOLT-4/N-Glycosidase F | 26 |
| 4.4. | Effect of reducing condition on binding | 26 |
| 5. | Optimising Purification | 27 |
| 5.1. | Immunoprecipitation | 27 |
| 5.2. | Ammonium Sulphate Fractionation | 30 |
| 5.3. | Hydrophobic Interaction Chromatography | 31 |
| 5.4. | Acetone precipitation | 32 |
| 6. | Sequencing and cloning | 33 |
| 6.1. | Amino acid sequence | 33 |
| 6.2. | DNA sequence cloning and sequencing | 33 |

1. General Description

The practice of the present invention will employ, unless otherwise indicated, conventional techniques of immunology, cytofluorimetry and molecular biology, which are within the skill of the art. Such techniques are explained fully in the literature (7).

The skilled person will understand and be familiar with the general methods and techniques of assay design and practice. The invention is described herein in sufficient detail for the skilled person to understand and repeat the experiments disclosed.

Standard abbreviations for virus and proteins are used in this specification. All publications, patents and patent applications cited herein are incorporated by reference. Envelope 1 (E1) and Envelope 2 (E2) of HCV refer to the proteins, and fragments thereof, the nucleotide sequence of which are published (EP-A-0318216 and EP-A-0388232 cited above). The nucleotides of the E1 and E2 genes and of the encoded proteins vary in different HCV isolates. Therefore, the E1 and E2 for any HCV isolates are identified because included in the amino acid sequences 192–383 and 384–750 respectively.

E1 and E2 have been produced by recombinant DNA techniques using different expression systems (Spaete et al and Chien et al cited above).

2. Cellular Assay 2.1. FACS Analysis of Cells Binding to E2

An experiment was performed with the aim of measuring the ability of HCV protein to bind to various cell types which should have the putative HCV receptor.

Cells ($10^5$/well) from the human T cell lymphoma, Molt-4 (commercially available and obtainable from the American Type Culture Collection), were pelleted in 96 U-bottom microplates (Costar) by centrifugation at 200× g for 5 minutes at 4° C. Twenty microliters of HcV proteins (CHO expressed recombinant E2 protein) diluted in PBS in different concentrations (from 10 $\mu$g/ml to 0.001 $\mu$g/ml) were mixed with the pellet of Molt-4 cells and incubated at 4° C. for 60 minutes. Non bound HCV proteins were removed by two centrifugations in PBS at 200× g for 5 minutes at 4° C.

Cells were subsequently incubated for 30 minutes at 4° C. with various dilutions (from 1/10 to 1/300000) of sera from humans, chimps, rabbits or mice that were either infected with HCV or have been immunised with HCV recombinant proteins or the corresponding pre-immune sera as control.

The cells were washed twice in PBS and incubated for 30 minutes with the appropriate dilutions of fluorescein-isothiocyanate-conjugated antisera (either to human IgG, or rabbit IgG, or mouse IgG).

Cells were subsequently washed in PBS at 4° C., resuspended in 100 $\mu$l PBS and cell-bound fluorescence was analyzed with a FCScan flow cytometer (Becton & Dickinson). By using a dot plot display of forward and side scatter, the machine is gated to include viable single cells and to exclude cell debris and clumps of cells. A total of 5000 events were collected and analyses of the data was done by using the Lysis II software program from Becton & Dickinson. This program produces histograms of each cell sample and calculates the mean channel fluorescence of the cell population, which directly relates to the surface density of fluorescently labelled HCV proteins bound to the cells.

Mean fluorescence values (mean channel number) of cells incubated with or without HCV proteins and with immune or preimmune sera were compared. The threshold for positivity is set for each experiment by flow cytometric analysis of cells without HCV proteins bound which have been incubated with antisera to HCV proteins and the FITC labelled second antibody. A representative binding experiment is shown in FIG. 1 which shows the separation achieved by flow cytometric analysis.

The experiment was also conducted with a variety of cell lines (for example haematopoietic cells other than MOLT-4 such as Jurkat, K562, Daudi, EBV-B (B-cell line transformed with Epstein-Barr virus and epithelial cells such as Hela, Adenocarcinoma and Huh 7) to identify cells capable of binding HCV proteins and therefore cells that have the putative receptor(s) for HCV following the protocol described above. It will be appreciated that repetition of this experiment is not necessary for the working of the present invention, but serves to prove the ubiquitous nature of the putative receptor (most of the cells are, in any event commonly available and were, in fact, obtained from the ATCC). The results were shown in FIG. 2, together with those for MOLT-4 and demonstrate that the specific binding of E2 to cells is widespread, suggesting that the HCV receptor is ubiquitous.

In a similar series of experiments, purified RA, purified RO, cord blood purif. RA, cord blood RA pha stim., KC3 TCC and SAG S9 TCC, which were tested for binding to recombinant HCV E2 protein expressed in CHO cells (E2-CHO) and found to bind confirming that binding occurs to non-transformed cell lines. The results are shown in FIG. 3.

2.2. Effect of E2 Modification on Binding

The effects of modifying the recombinant HCV protein E2, expressed in CHO cells (E2-CHO) on binding to MOLT-4 cells were investigated using a reducing agent and a deglycosylating enzyme.

2.2.1. E2 Reduction

25 $\mu$l of E2-CHO SMC-PC (130 $\mu$g/ml) in 20 mM potassium phosphate, 0.1 M NaCl, pH 6.0 were buffered at pH 8.0 with 1M Tris-base (total 1 $\mu$l) and then added with BSH (beta mercaptoethanol) to a final concentration of 500 mM; tubes were flushed with nitrogen and the reaction allowed to proceed for 100 minutes at 37° C.

Samples from above were diluted 1:20 with RPMI medium and used for a FACS binding assay with MOLT-4 cells as described above. The final concentration of BSH in the FACS assay was 12.5 mM and under these conditions, cells were verified to be alive in previous preliminary experiments (over 90% of cells still alive at 50 mM BSH).

Figure 4:
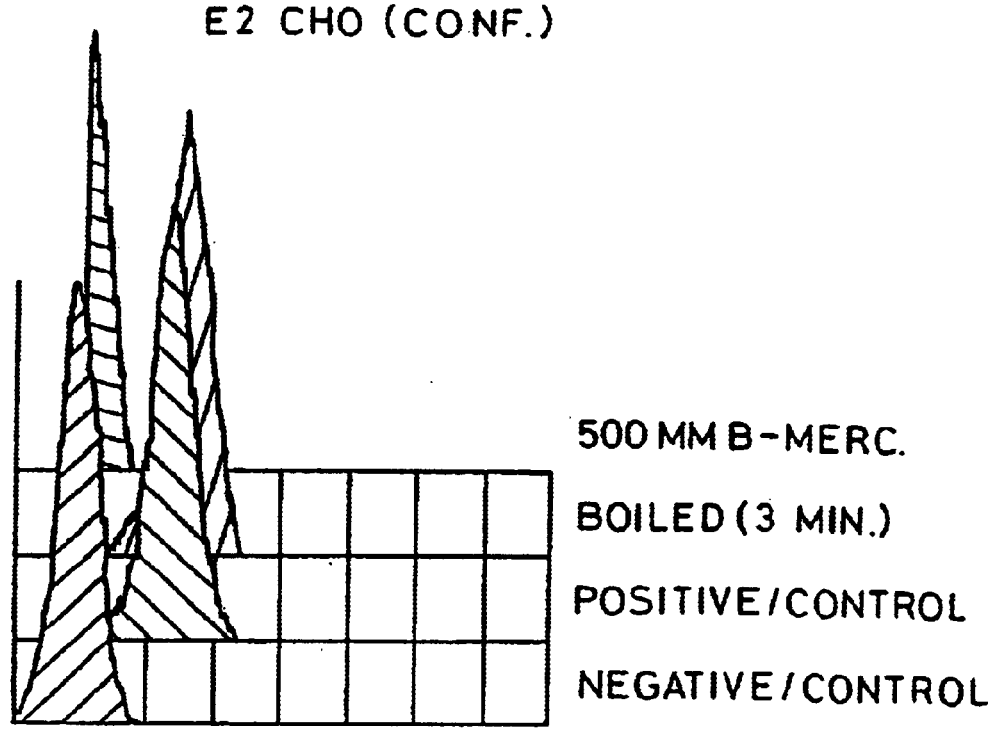
FIG. 4 is a set of computer-generated histograms depicting the results of a FACScan analysis of the binding of E2 CHO to MOLT-4 cells with and without treatment with beta mercaptoethanol (BSH) an S—S linkage reducing agent (filled curve unlabelled control, open curve labelled). The plot is of cell population against fluorescence intensity.

The results in FIG. 4 show that binding of MOLT-4 cells to recombinant E2 is substantially reduced on reduction with beta-mercaptoethanol, indicating a requirement for a correct E2 conformation maintained by S—S bridges.

2.2.2. E2 Deglycosylation

25 $\mu$l of E2-CHO SMC-PC (130 $\mu$g/ml) in 20 mM potassium phosphate, 0.1 M NaCl, pH 6.0 were added with 30 $\mu$l of 0.2 M $NaH_2PO_4$ to a final pH of 5.5 plus SDS to a final concentration of 0.01%. Then 10 $\mu$l of Endo-H stock was added to a final concentration of 200 mU/ml keeping the pH constant and the resulting sample was kept at 37° C. for 20 hours. The sample was then diluted 1:20 with RPMI and used for in a FACS binding assay as described above.

Figure 5:
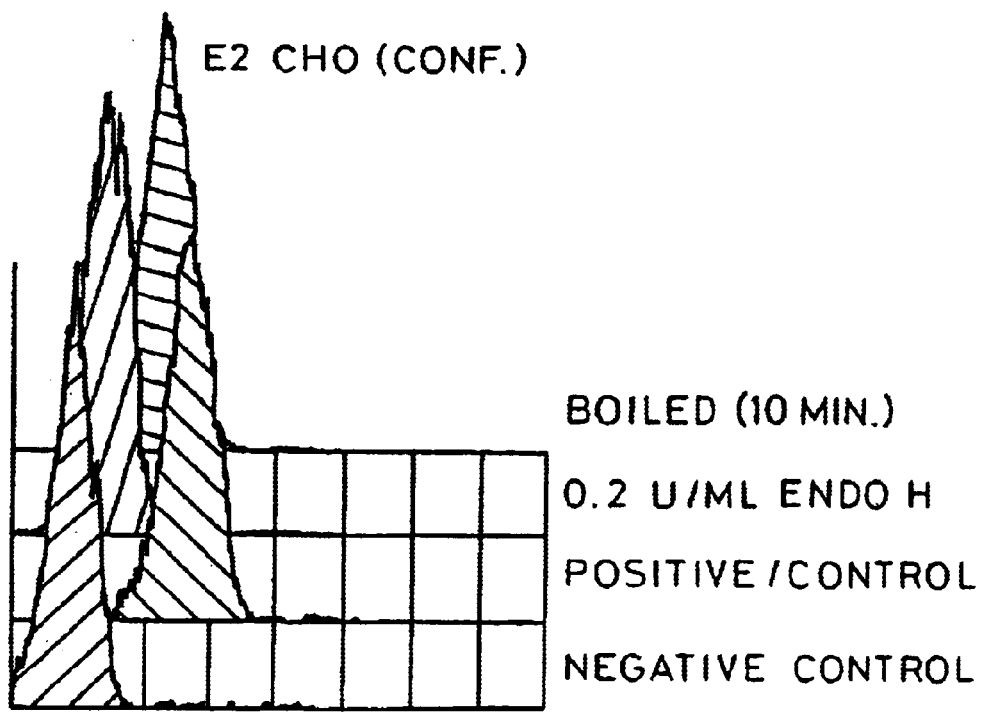
FIG. 5 is a set of computer-generated histograms depicting the results of a FACScan analysis of the binding of E2 CHO to MOLT-4 cells with and without treatment with Endo-H, a deglycosylating enzyme (filled curve unlabelled control, open curve labelled). The plot is of cell population against fluorescence intensity.

The results in FIG. 5 show that binding of MOLT-4 cells to recombinant E2 is substantially reduced on deglycosylation with Endo-H, indicating a requirement for glycosylation of E2 for binding.

2.3. Monoclonal Antibody Production

Monoclonal antibodies were prepared using standard procedures and by immunising mice with recombinant HCV E2 produced in CHO cells (E2-CHO). Several cell lines were established which were capable of binding to E2-CHO as were cell lines capable of binding to E2 bound to MOLT-4 cells and cell lines capable of neutralising the binding of E2-CHO to MOLT-4 cells.

3. Preparation of 24 kd Putative Receptor 3.1. 24 kd Protein Preparation from MOLT-4 Cells The 24 kd protein was purified from MOLT-4 cells by membrane purification and by plasma membrane purification, the latter giving the better yield of protein.

3.1.1. Membrane Purification

MOLT-4 cells were grown at 37° C., 5% $CO_2$ in RPMI buffered with 25 mM Hepes in a growth medium containing Fetal Calf Serum (FCS—final concentration 5%), 1 mM glutamine, 100 µg/ml kanamicin, MEM vitamins (Gibco), 1 mM sodium pyruvate, MEM non essential amino acids (Gibco), $5 \times 10^{-5}$ M β-mercaptoethanol.

Cells were harvested after reaching a density of 750,000–1,000,000 cells per ml.

The growth medium containing cells was centrifuged at 300 g for 10 minutes to pellet down the cells. Pelleted cells were washed three times in PBS Buffer (resuspended and recentrifuged).

The cell pellet was resuspended in hypotonic solution at 1 ml of hypotonic solution per $100 \times 10^6$ cells.

The hypotonic solution contained Tris (10 mM), NaCl (10 mM), $CaCl_2$ (0.2 mM), $MgCl_2$ (1.5 mM), PMSF (1.0 mM), aprotinin (2.0 µg/ml), pepstatin (0.7 µg/ml) and leupeptin (0.5 µg/ml).

Cells were left at 4° C. under gentle shaking for 20 minutes and then disrupted with 25 strokes of a Potter manual homogenizer.

Membranes were recovered after sequential centrifugation of the supernatant at 100 g for 7 minutes, 3500 g for 10 minutes and 40,000 g for 60 minutes. The pellet obtained from the above was dissolved in suitable buffer.

The buffer used for dissolution of the 40,000 g membrane pellet contained 1% Triton X-100 in PBS buffer pH 7.4, 8 mM Chaps in PBS buffer pH 7.4 and 4 M Urea in sodium phosphate buffer pH 7.4.

All the buffers used for membrane solubilisation contained protease inhibitors at the concentrations reported above for the hypotonic solution and were used at a ratio of 200 µl of buffer per $5 \times 10^8$ cells.

Solubilised material was centrifuged at 100,000 g for 60 minutes and the supernatant kept for further use after estimation of protein content by BCA method.

The material obtained was subjected to analyses as described below.

3.1.2. Plasma Membrane Purification

The procedure for plasma membrane purification was based on Morre' D. J. et al. (8).

MOLT-4 cells were grown at 37° C., 5% $CO_2$ in RPMI buffered with 25 mM Hepes in a growth medium containing Fetal Calf Serum (FCS—final concentration 5%), 1 mM glutamine, 100 µl/ml kanamicin, MEM vitamins (Gibco), 1 mM sodium pyruvate, MEM non essential amino acids (Gibco), $5 \times 10^{-5}$ M β-mercaptoethanol.

Cells were pelleted from culture medium and washed three times with PBS.

The pelleted cells were resuspended in 0.2 mM EDTA, 1 mM $NaHCO_3$ containing the following protease inhibitors: PMSF (1.0 mM), aprotinin (2.0 µg/ml), pepstatin (0.7 µg/ml), leupeptin (0.5 µg/ml) at a ratio between buffer and cells of 2 ml per each $10^8$ cells.

Resuspended cells were disrupted with a Polytron homogenizer using an S25 N10 G probe for 40 seconds at 9500 rpm. Cell disruption was verified by optical microscope. The homogenate was centrifuged at 300 g and the resulting supernatant further centrifuged at 23,500 g for 60 minutes. The resulting pellet was resuspended in 0.2 M potassium phosphate pH 7.2 containing protease inhibitors in the ratios described above. The buffer volume was 1 ml each $5 \times 10^8$ cells.

The membrane suspension was partitioned across the following two phase system:

| | |
|---|---|
| 20% (w/w) T500 Dextran | 13.2 g |
| 40% (w/w) PEG 3350 | 6.6 g |
| 0.2 KP, pH 7.2 | 0.8 ml |
| membrane susp. | 5.0 g |
| Distilled water | up to 35 g |

The sample as chilled at 4° C. and the tubes were inverted 30 to 40 times keeping the temperature constant. The sample was then centrifuged on a swinging bucket rotor at 150–200 g for 5 minutes at 4° C. The upper phase was removed and five-fold diluted with 1 mM sodium bicarbonate containing protease inhibitors. The membranes were collected by centrifugation at 30,000 g for 30 minutes.

The pellet was dissolved in a suitable buffer and centrifuged at 100,000 g for 60 minutes to eliminate undissolved material.

The material obtained was subjected to analyses as described below.

3.2. Hyperexpressing MOLT-4 Cells

A further cell line capable of hyperexpression of the characteristic binding ability for E2 was prepared by selecting and recloning MOLT-4 cells binding E2 strongly. The resulting cell-line showed a markedly greater binding affinity for E2 than the wild-type strain.

4. Characterisation of Receptor

4.1. Western Blot Protocol

The following experiments demonstrate binding of E2 to purified 24 kd protein in a western blot of proteins from MOLT-4 cells purified from membranes and from plasma membranes and from peripheral blood mononuclear cells (PBMC).

Unless otherwise indicated, all SDS-PAGE experiments were performed according to Laemmli et al (9), samples of solubilised membranes were run under non-reducing conditions and without boiling before each electrophoretic run.

After electrophoretic transfer (Western blot) in buffer containing 25 mM Tris, 192 mM glycine, 20% methanol at constant electric field of 10 Volts/cm, blotted transfer supports were saturated for 2 hours in PBS buffer pH 7.4 containing 0.05% Tween 20 and 10% powdered skimmed milk at room temperature. After $1 \times 15$ minutes and $2 \times 5$ minutes, washes in PBS, 0.05% Tween 20 containing 1% powdered skimmed milk, transfer supports were incubated overnight with E2-CHO recombinant protein at a concentration of 1–2 µg/ml dissolved in PBS buffer containing 0.05% Tween 20, 1% milk, 0.02% sodium azide. Negative control transfer supports (blotted with the same samples) were incubated for the same time in the same buffer without E2-CHO protein.

To detect E2-CHO recombinant protein bound to the transfer supports, these were incubated with the culture supernatant of an hybridoma named 291A2 (a monoclonal antibody that recognises epitopes exposed on E2 when bound to its putative receptor) at 1:500 dilution in PBS, Tween 0.05%, milk 1% for 2 hours.

After this step, transfer supports were washed $1 \times 15$ minutes and $2 \times 5$ minutes with PBS Tween 0.05% milk 1% solution. Transfer supports were then incubated for 1 hour with biotin conjugated goat anti-mouse immunoglobulin specific polyclonal antibody of commercial source (PharMingen, San Diego, Calif., USA) at 1:2000 dilution in the PBS/Tween/Milk solution mentioned above. After this step, transfer supports were washed $1 \times 15$ minutes and $2 \times 5$ minutes with PBS/Tween/Milk. Finally transfer supports were incubated for 1 hour with Extravidin™-Peroxidase (Sigma Immunochemicals Co., St Louis, Mo., USA) at 1:2500 dilution in PBS/Tween/Milk. Transfer supports were then washed 1×15 minutes and 4×5 minutes with PBS buffer pH 7.4 containing 0.05% Tween 20. Chemiluminescent staining was performed using ECL™ western blotting detection reagents (Amersham, UK).

4.1.1. Membrane Proteins

A membrane preparation was prepared as described above.

Membrane pellets resulting from 40,000 g centrifugation were dissolved in buffers reported below and centrifuged at 100,000 g to remove undissolved material. Pellets were reextracted with 1% Triton X-100 in PBS pH 7.4.

Following SDS-PAGE (15 μg/lane) and blotting, the transfer supports were incubated with E2-CHO recombinant protein as described above.

Figure 6:
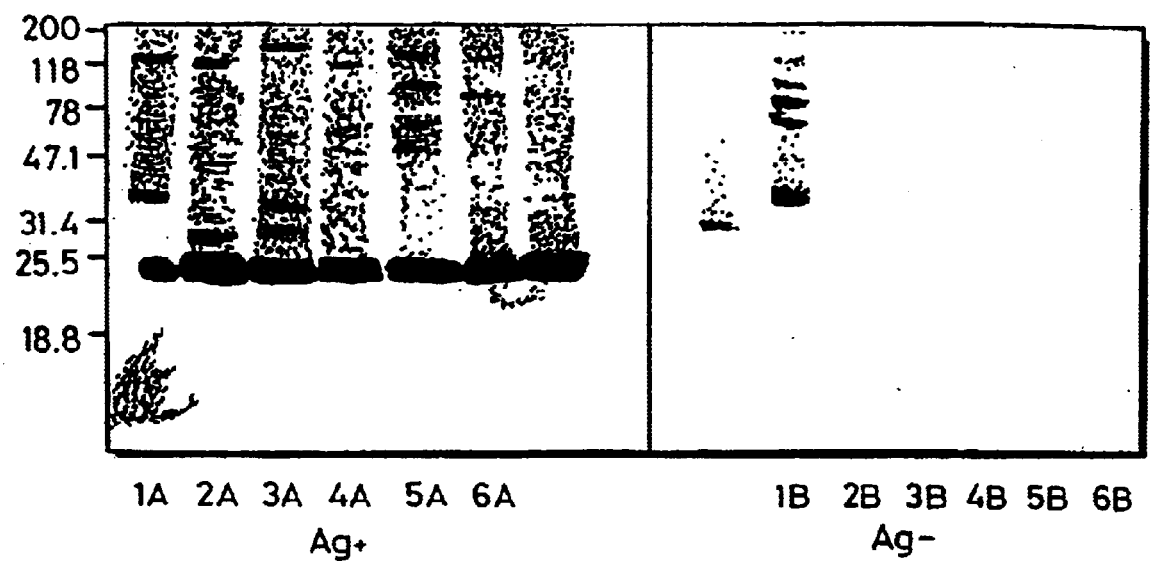
FIG. 6 is a western-blot of membranes prepared from MOLT-4 cells and solubilized in different buffers (see page 22 for lane descriptions).

The results are shown in FIG. 6.

| Lane | Description |
| --- | --- |
| 1A | 4M Urea in 50 mM sodium phosphate pH 7.2 |
| 2A | Pellet from lane 1A sample solubilized in 1% Triton X-100 in PBS pH 7.4 |
| 3A | 1% Triton X-100 in PBS pH 7.4 |
| 4A | Pellet from lane 3A sample solubilized in 1% Triton X-100 in PBS pH 7.4 |
| 5A | 0.01% Triton X-100 in PBS pH 7.4 |
| 6A | Pellet from lane 5A sample solubilized in 1% Triton X-100 in PBS pH 7.4 |

1B to 6B are negative controls for the corresponding samples in lanes 1A to 6A.

The protein band at 24 kd is clearly visible.

4.1.2. Plasma Membrane Proteins

A plasma membrane preparation was prepared as described above.

Plasma membranes were solubilized in PBS pH 7.4 containing 1% Triton X-100 and subjected to Laemmli SDS-PAGE. The transfer support was incubated with E2-CHO recombinant protein.

Figure 7:
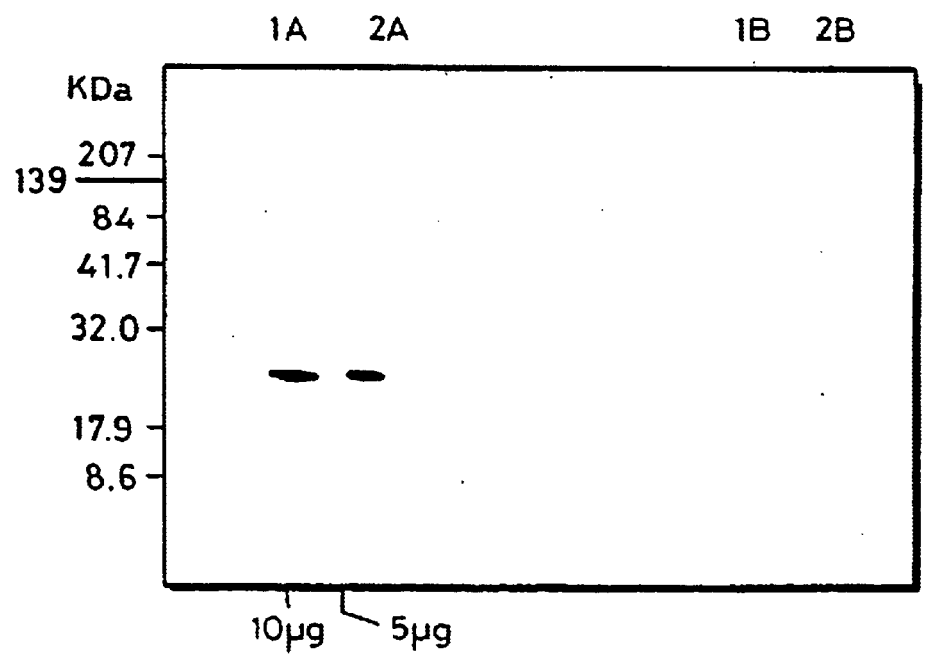
FIG. 7 is a western blot of plasmatic membrane from MOLT-4 cells (see page 23 for lane descriptions).

The results are shown in FIG. 7.

| Lane | Description |
| --- | --- |
| 1A | plasma membranes, 10 μg total protein content |
| 2A | plasma membranes, 5 μg total protein content |

Lanes 1B and 2B are negative controls for the corresponding samples in lanes 1A and 2A.

The protein band at 24 kd is clearly visible.

4.1.3. Western Blot of PBMC Cells

To assess whether the 24 kd protein could be identified in normal cells a sample of peripheral blood mononuclear cells was purified using the procedure described above and subjected to western blotting as described above.

Figure 8:
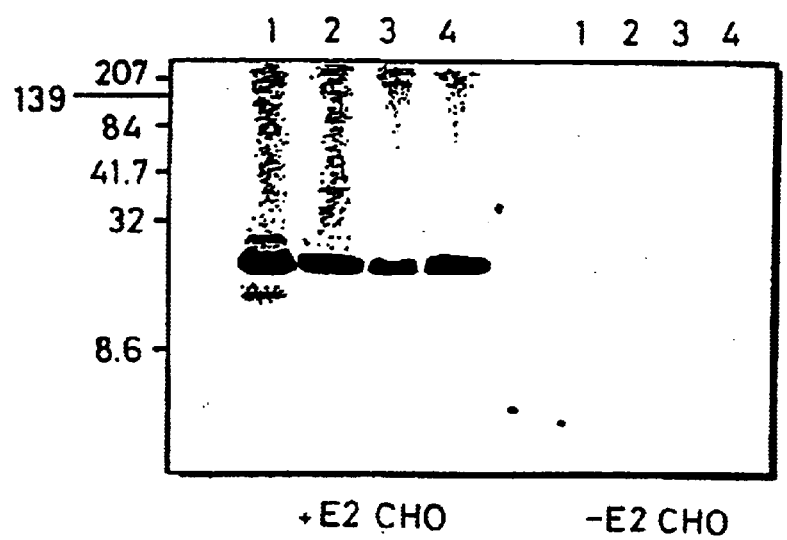
FIG. 8 is a western blot of MOLT-4 and PBMC membrane proteins (see page 23 for lane descriptions).

The results are described in FIG. 8.

| Lane | Description |
| --- | --- |
| 1/2 | Molt-4 membrane proteins |
| 3 | PBMC membrane proteins (22 μg/ml) |
| 4 | PBMC membrane proteins (44 μg/ml) |

The negative control lanes are marked "−E2 CHO"

4.2. Cell surface Expression of Receptor

Employing the protocols described above, various cell types were analysed using FACscan and western blotting for the presence of the 24 kd protein putative HCV receptor.

The results are depicted below:

|  |  | FACS | W B | HCV |
| --- | --- | --- | --- | --- |
| T and B lympho | human | +++ | +++ | +++ |
| Monocytes | human | +++ |  | +++ |
| HeLa | human | ++ |  | +++ |
| Gastric carcinoma | human | ++ |  | +++ |
| Hepatoma cells | human | +++ | +++ | +++ |
| Myoblastoma | human | + |  | − |
| Fresh liver cells | Green monkeys | − | − | − |
| Lymphomonocytes | rabbit | − |  | − |
| Fresh liver cells | rabbit |  | − | − |
| Any cells | mouse |  | − | − |

These results demonstrate that the species distribution of the 24 kd protein matches that of HCV infection susceptibility.

4.3. Effect of Enzymes on 24 kd Protein Binding 4.3.1. Flow Cytometry

The biochemical nature of the cell surface component (receptor) that mediates attachment of E2 CHO envelope protein to Molt 4 cells was investigated. Pretreatment of Molt 4 cells with *V. cholerae* neuraminidase, which has a α-2,3 specificity does not reduce E2 CHO binding.

The proteinaceous nature of the receptor was demonstrated when cells pretreated with proteases abolished binding capability of E2 CHO whereas phospholipase treatment of cells did not affect the binding, suggesting that the cellular attachment proteins were not glycosylphosphatilylinositol anchor linked. The E2 binding site on Molt 4 cells was sensitive to all protease used, which included both serine proteases, such as trypsin, and a thiol protease, such as papain.

The results of proteolytic treatment demonstrated the involvement of membrane proteins in envelope protein binding and were as follows:

| Treatment | Concentration | Fluorescence intensity (% of control) |
| --- | --- | --- |
| Control |  | 100 |
| Pronase E | 10 μg/ml | 36 |
| Pronase E | 100 μg/ml | 34 |
| Trypsin | 100 μg/ml | 33 |
| Papain | 100 μg/ml | 42 |
| Phospholipase C (from *Bacillus cereus*) | 3 U/ml | 100 |
| Phospholipase C | 25 U/ml | 96 |
| Neuraminidase | 50 mU/ml | 100 |

Cells ($10^6$ ml$^{-1}$) were incubated for 60 min at 37° C. in RPMI 1640/Hepes medium plus the enzymes indicated above. The cells were centrifuged, resuspended in fresh medium and incubated with E2 CHO protein (3 μg/ml). Purified anti E2 CHO monoclonal antibody (1.5 μg/ml) was used as a second step. Purified phycoerythrin-labelled rabbit anti mouse antibody (5 μg/ml) was used as a third step reagent. A total of 5000 cells per sample was evaluated with a FACScan flow cytometer.

Enzymes were used at a concentration that did not affect cell viability as measured by propidium iodine exclusion during FACS analysis.

Fluorescence was recorded as arbitrary units (channel numbers) on a logarithmic scale and median intensities determined. Data from individual experiments were normalized with respect to the fluorescence of unstained control samples and value are expressed as percentages of the fluorescence intensities in the stained control samples.

4.3.2. Western Blot on MOLT-4/N-Glycosidase F

Peptide N-Glycosidase F treatment was performed incubating membrane proteins (50 µg) overnight at 37° C. in phosphate buffer pH 7,4,25 mM EDTA plus enzyme (50 U/ml) and successively loaded on 12% SDS PAGE.

To show the activity N-Glycosidase F enzyme (PNGase F), as control, gp 120 polypeptide was used in the same experiment (data not shown).

Figure 9:
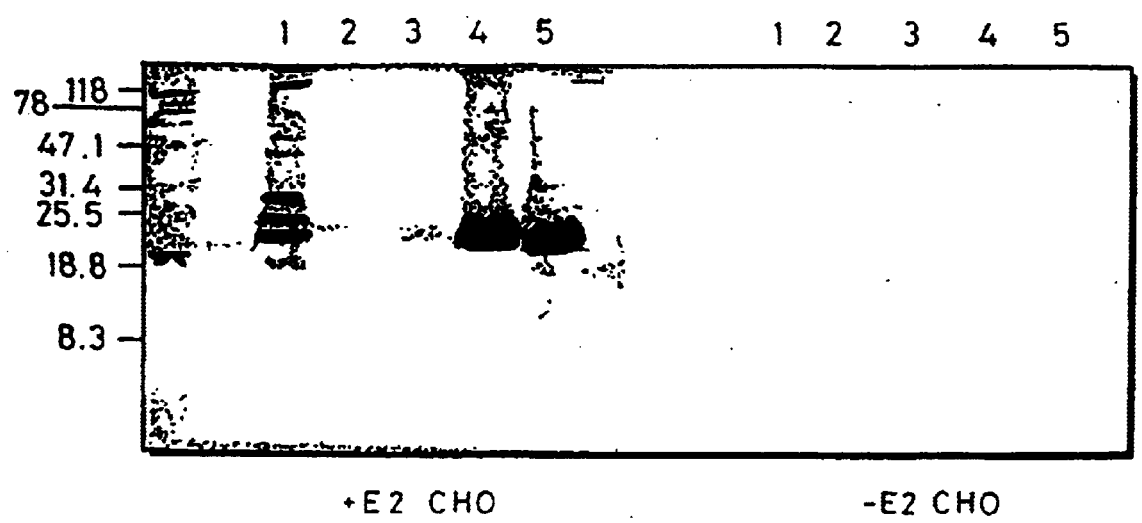
FIG. 9 is a western blot of MOLT 4 cells membrane proteins treated with N-Glycosidase F (see page 26 for lane descriptions).

The results are shown in FIG. 9.

| Lane | Description |
| --- | --- |
| 1 | +/ve control |
| 2 | treated and boiled membrane |
| 3 | untreated and boiled membrane |
| 4 | treated membrane |
| 5 | untreated membrane |

These results show that treatment of a MOLT 4 membrane preparation with Peptide-N-glycosidase F, which hydrolyzes all N-linked glycanes, does not abolish E2 CHO binding.

4.4. Effect of Reducing Condition on Binding

A western blot of MOLT-4 and COS-7 membranes, prepared as described above, were electrophoresed in reducing and non reducing conditions to establish the requirement or otherwise for disulphide bridges in the 24 kd protein, by measuring the binding of E2-CHO to the transfer support.

Transfer supports were incubated with E2-CHO recombinant protein as described above.

Figure 10:
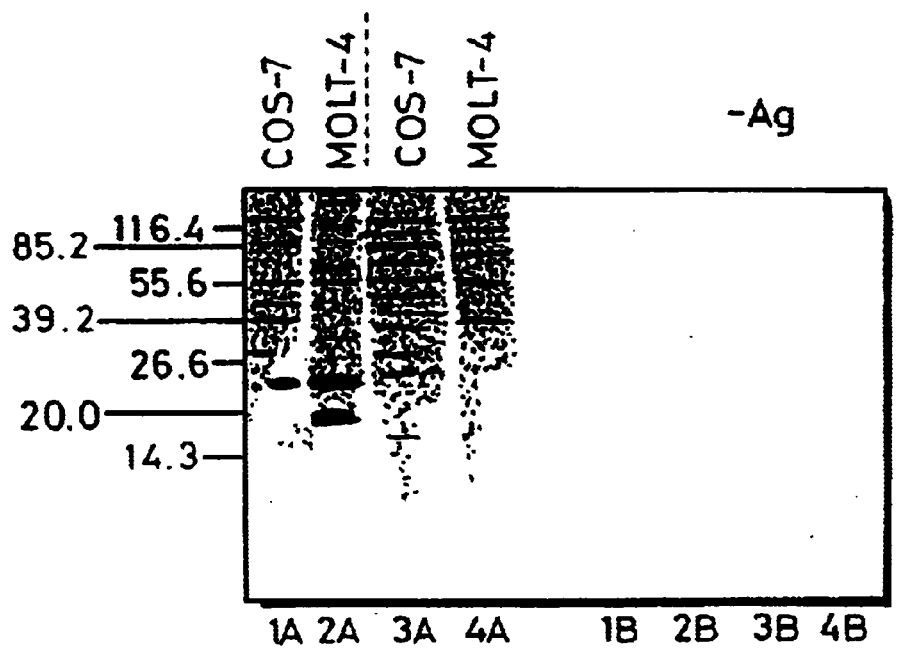
FIG. 10 is a western Blot of MOLT-4 and COS-7 membranes electrophoresed in reducing and non reducing conditions (see page for 27 lane descriptions).

The results are shown in FIG. 10.

| Lane | Description |
| --- | --- |
| 1A | COS-7 membranes in non reducing SDS Laemmli buffer |
| 2A | MOLT-4 membranes in non reducing SDS Laemmli buffer |
| 3A | COS-7 membranes in SDS Laemmli buffer containing 5% β-SH |
| 4A | MOLT-4 membranes in SDS Laemmli buffer containing 5% β-SH |

1B to 4B are negative controls for the corresponding lanes 1A to 4A.

5. Optimising Purification 5.1. Immunoprecipitation

Membrane Proteins Solubilization

A membrane preparation from 400 million MOLT-4 cells (A2A6 subclone) was treated with 200 µl of PBS buffer, pH 7.4, containing CHAPS 7.5 mM and the following protease inhibitors in µl/ml: PMSF 35, aprotinin 2, pepstatin 0.7, leupeptin 0.5. After treatment with the above buffer, the resulting suspension was centrifuged at 100,000 g for 1 hour and the clear supernatant underwent immunoprecipitation experiments. The final protein concentration based on BCA protein assay (Pierce, USA) was 2.7 mg/ml.

Incubation with E2 Recombinant Envelope Protein

200 µl of membrane protein solution (2.7 mg/ml) in PBS-CHAPS were added to 15 µl of CHO-produced E2 (Batch P4) solution. The stock concentration of E2-P4 protein was 130 µl/ml and its final concentration in the protein membrane solution was 9.75 µg/ml.

The mixture was kept overnight under stirring at 4° C.

Incubation with Rabbit Anti-E2 Antisera

The resulting solution was divided into two aliquots of 100 µl and each was mixed with 5 µl of preimmune and postimmune antiserum from a rabbit (R#1) previously immunized with E2 protein. The final dilution of antisera was 1:20. Incubation was performed for 1 hour at 4° C.

Addition of Protein-A Sepharose CL-4B

Protein-A Sepharose CL-4B resin (Pharmacia, Sweden) was extensively washed with PBS containing 7.5 mM CHAPS at pH 7.4, and 30 µl of compact slurry (capacity of matrix is 20 mg of human Ig per ml of slurry) were added to each 100 µl sample resulting from the step above. Incubation was performed under stirring for 1 hour at 4° C.

The samples were centrifuged to pellet down the resin and the supernatant was removed, mixed with Laemmli-Buffer (without reducing agent) and kept for SDS-PAGE. The resin pellet was washed twice with 500 µl of PBS-CHAPS (10 min each wash at 4° C.) and then the pellet was treated with 50 µl of Laemmli Buffer containing 5M urea. The resulting supernatant was subjected to SDS-PAGE.

SDS-PAGE and Immunoblot

The samples from the steps above, that is, supernatant containing material not absorbed on Protein-A matrix (SN) and material desorbed from Protein-A matrix (ProtA) from both preimmune and postimmune antisera, were loaded on SDS-PAGE gel in non reducing buffer and without heating. After the run, the gels were electroblotted on nitrocellulose paper in 20% methanol Tris-Glycine buffer and were subjected immunostaining as described above. Incubation with E2 protein was performed overnight using E2 SMC-PC at 1.73 µg/ml in PBS 0.05% Tween 20.1% milk.

The samples loaded on SDS-PAGE were:

A) Supernatant (material not retained by Prot-A) from Preimmune antiserum,

B) Prot-A desorbed material from PREimmune antiserum,

C) Supernatant from POSTimmune antiserum, and

D) Prot-A desorbed material from POSTimmune antiserum

Three sets of these samples were loaded on gel, one was stained directly on gel the other two underwent immunostain, one incubated with E2 the other as negative control.

The nitrocellulose transferred support was incubated with E2-CHO SMC-PC recombinant protein at 1.73 µg/ml followed by 291A2 hybridoma culture supernatant (containing a monoclonal antibody that recognises epitopes exposed on E2 when bound to its putative receptor), biotinylated polyclonal anti-mouse Ig antibodies and peroxidase labelled Extravidin™ (Sigma Immunochemicals, USA). Chemiluminescent staining obtained with ECL-Luminol (Amersham, GB), exposure 1 minute.

Figure 11:
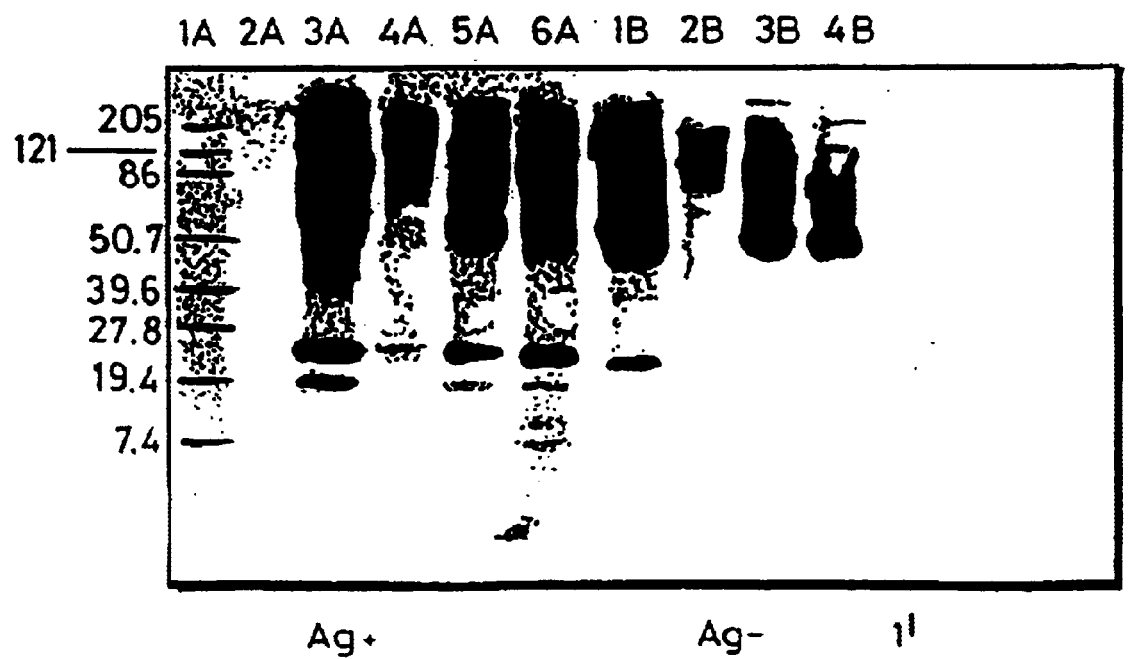
FIG. 11 is a western blot of an experiment demonstrating immunoprecipitation of an E2-CHO/putative receptor complex (see page 29 for lane descriptions).

The results are shown in FIG. 11.

| Lane | Description |
| --- | --- |
| 1A | molecular weight standard |
| 2A | empty |
| 3A | sample incubated with preimmune rabbit serum - supernatant |
| 4A | sample incubated with preimmune rabbit serum - Protein-A bound |
| 5A | sample incubated with postimmune rabbit serum - supernatant |
| 6A | sample incubated with postimmune rabbit serum - Protein-A bound |

The negative controls employed the nitrocellulose membrane incubated with 291A2 hybridoma culture supernatant followed by biotinylated polyclonal anti-mouse Ig antibodies and peroxidase labelled streptavidin. 1B to 4B correspond to 3A to 6A respectively.

5.2. Ammonium Sulphate Fractionation

Membranes were prepared as reported in the membrane preparation protocol from MOLT-4 cells and solubilized in PBS buffer pH 7.4 containing 8 mM CHAPS. The protein concentration estimated on the basis of BCA assay ranges from 1.8 and 2.5 mg/ml.

Solubilized membranes were mixed with an ammonium sulphate (AS) saturated solution in a volume sufficient to obtain 25% saturation of ammonium sulphate (i.e. the final concentration of AS is 25% of the starting saturated solution). The sample was allowed to stand in melting ice for 2 hours and then centrifuged at 15800 g for 30 minutes.

The supernatant was mixed with AS saturated solution to a final saturation of 50%. The sample was allowed to stand for 2 hours on melting ice and then filtered on a Spin-X™ centrifuge filter unit (Costar, Cambridge, Mass., USA) for 15 minutes at 4° C.

The precipitates obtained above were dissolved in suitable buffers and undergo further treatment.

The pellets were redissolved in PBS pH 7.4 containing 10M urea and underwent Laemmli SDS-PAGE. The volumes of AS fractions were loaded in such a way that the amount of putative receptor should be comparable in different samples.

The transfer support was incubated with E2-CHO recombinant protein as described above.

Figure 12:
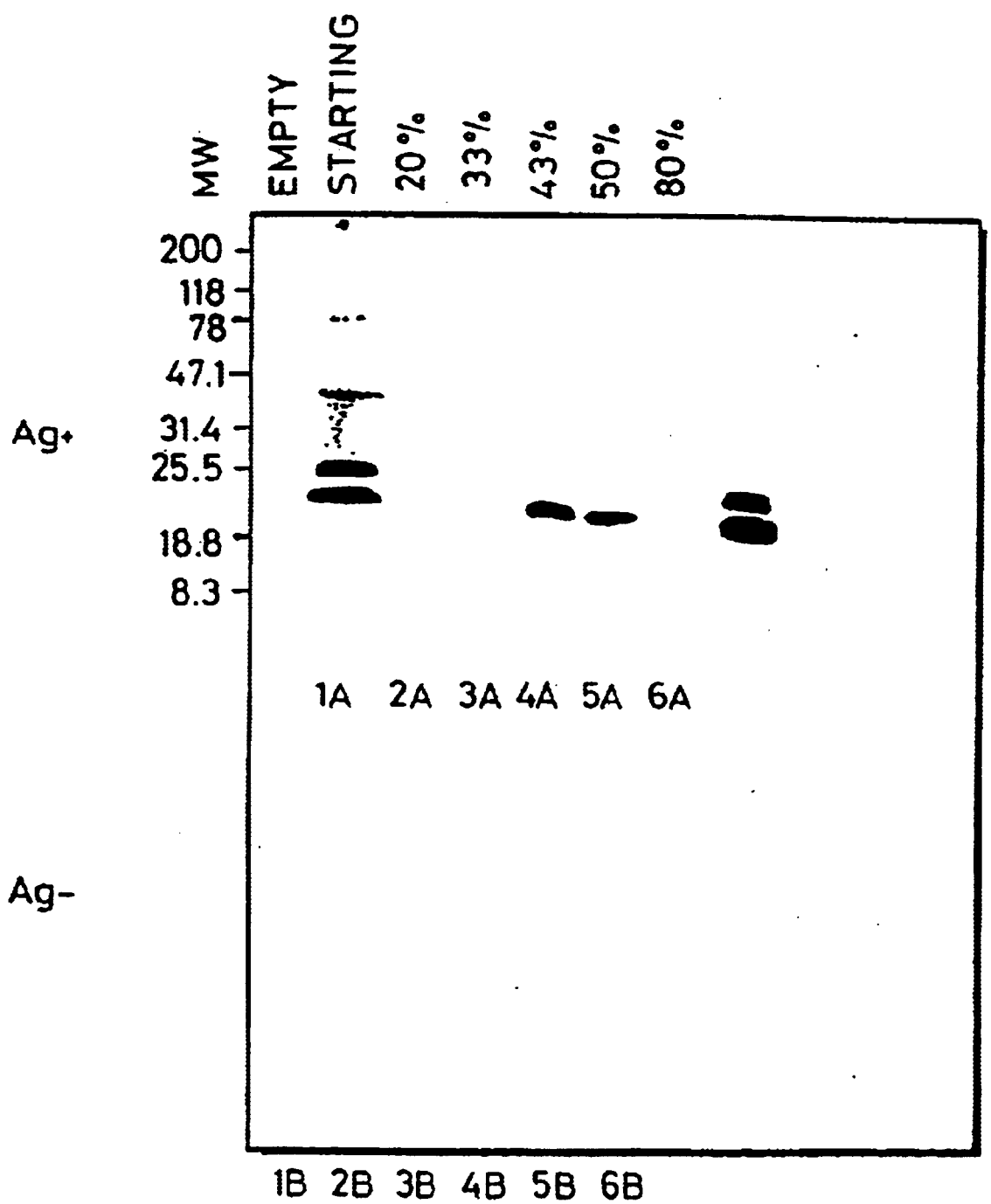
FIG. 12 is a western blot of ammonium sulphate fractions from MOLT-4 cells membranes (see page 31 for lanes).

The results are shown in FIG. 12 and show that precipitation of p24 occurs in the range of 33 to 50% of saturation.

| Lane | Description |
| --- | --- |
| 1A | Starting membranes |
| 2A | 20% AS fraction |
| 3A | 33% AS fraction |
| 4A | 43% AS fraction |
| 5A | 50% AS fraction |
| 6A | 60% AS fraction |

5.3. Hydrophobic Interaction Chromatography 1.5 ml of solubilized membranes from MOLT-4 cells (protein concentration 2.5 mg/ml) were pre-fractionated at 25% of saturation of ammonium sulphate and the supernatant from this step was brought to 50% saturation of AS. The precipitate obtained was resuspended in 200 µl of PBS containing ammonium sulphate at 25% of saturation. The undissolved material was pelleted by centrifugation at 15800 g for 30 minutes. The supernatant obtained was incubated with 200 µl of Phenyl-Sepharose matrix (Pharmacia, Uppsala, Sweden), previously equilibrated in PBS pH 7.2 containing AS at 25% of saturation, for 2 hours at room temperature.

The non retained material was recovered by filtering on a Spin-X™ centrifuge filter units (Costar, USA).

The matrix of Phenyl-Sepharose was washed twice with 100 µl of PBS, 25% AS saturation and once with 300 ml of the same buffer. The matrix was then eluted with PBS pH 7.4 (200 µl) and then with PBS, pH 7.4 containing 20 MeOH. Finally, the matrix was treated with 40 µl of non reducing Laemmli buffer.

Samples containing ammonium sulphate (i.e. non retained and wash material) were dialysed against 8M urea in PBS, pH 7.4.

All samples underwent SDS-PAGE analysis and Western Blot.

5.4. Acetone Precipitation

50 µl of membranes from MOLT-4 cells solubilized in 8 mM CHAPS in PBS, pH 7.4 were mixed with 200 µl of acetone.

The sample was centrifuged at 15800 g for 15 minutes and the supernatant was discarded. The obtained precipitate was dissolved in non reducing Laemmli sample buffer and underwent SDS-PAGE and Western Blot. The transfer supports incubated with E2-CHO recombinant protein as described above.

Figure 13:
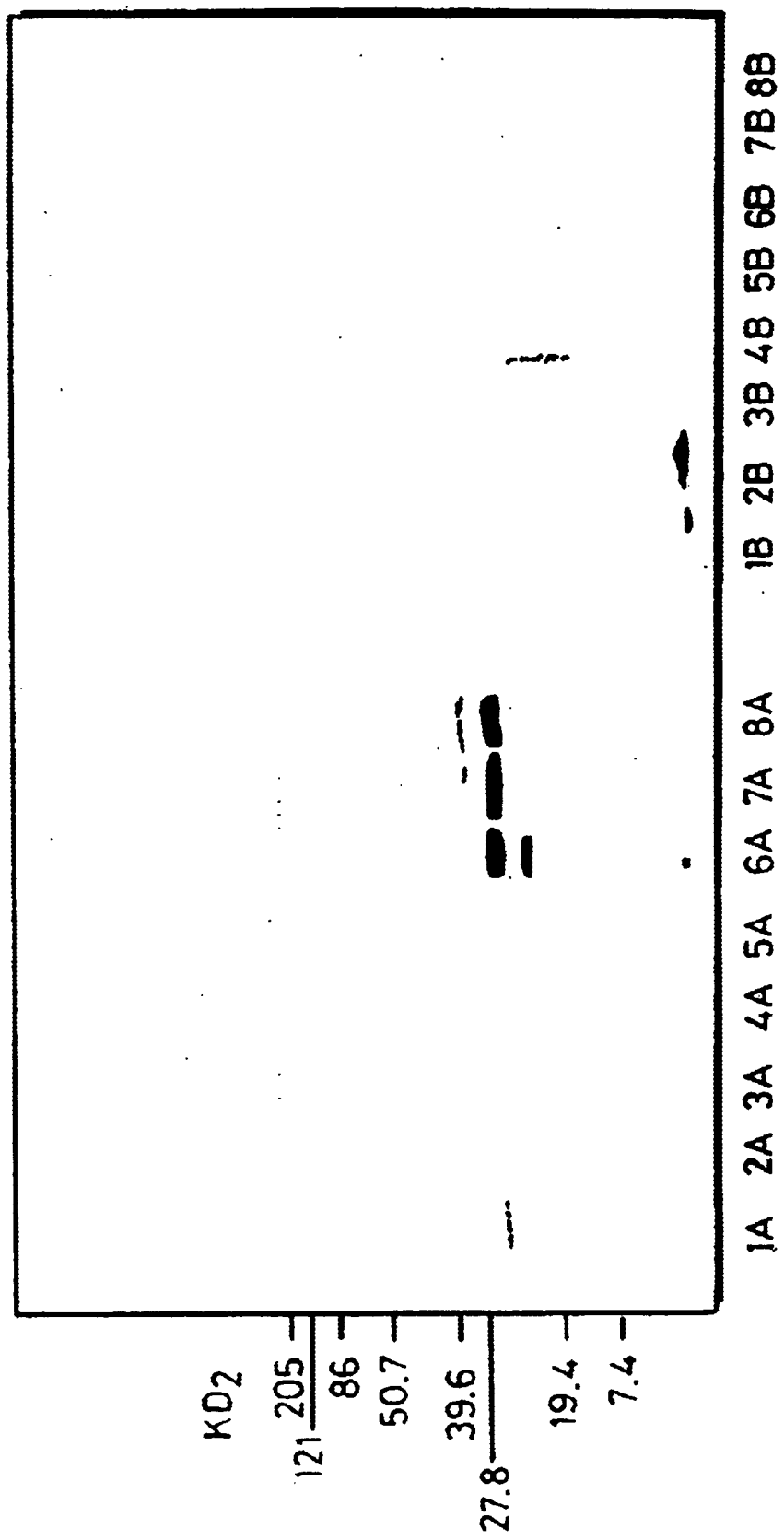
FIG. 13 is a western blot of samples from a hydrophobic interaction chromatography experiment with an acetone precipitation step (see page 32 for lanes).

The results of the combined HIC and acetone precipitation experiment are shown in FIG. 13.

| Lane | Description |
| --- | --- |
| 1A | Starting membranes (16 µl total protein content) |
| 2A | material non retained on matrix |
| 3A | wash |
| 4A | material eluted with PBS, pH 7.4 |
| 5A | material eluted with PBS, pH 7.4 containing 20% Methanol |
| 6A | material eluted with Laemmli Buffer |
| 7A | membranes solubilized in Triton 1% PBS, pH 7.4 (26 µg total protein) |
| 8A | acetone precipitate from sample 7A |

Samples from 1B to 8B correspond to samples from 1A to 8A

These experiments show that ammonium sulphate precipitated material can be redissolved in suitable conditions and undergo hydrophobic interaction chromatography. The 24 kd HCV putative receptor protein binds to Phenyl Sepharose and can be recovered from this matrix.

The membrane extract can be precipitated with acetone without loss of binding capacity of HCV putative receptor.

6. Sequencing and Cloning

6.1. Amino Acid Sequence

The amino acid sequence of the 24 kd protein may be elucidated either by inference from the cloned DNA or by microsequencing of protein prepared by one of the processes described above. Based upon the molecular weight of the protein (and the knowledge that, if glycosylated it is only glycosylated to a small extent) it is expected that the protein will have approximately 210–230 amino acids (allowing the average of 110 daltons per amino acid).

6.2. DNA Sequence Cloning and Sequencing

The DNA sequence of the 24 kd protein may be determined by one of a number of techniques known to the art, such as λgt11 "shotgun" cloning where a DNA library is produced, suitably from a hyperexpressing cell-line (see above) and fragments of DNA were caused to express in prokaryotic or eukaryotic cell, the products being screened using antibodies to the 24 kd protein or by binding to recombinant E2-CHO.

Once identified, the DNA encoding the 24 kd protein may be used to produce large quantities of the protein which, as a result of its binding to HCV may prove useful in an assay for HCV infection or for the manufacture of a medicament for treating HCV infection.

Alternatively, the DNA may be used to prepare transgenic animals bearing the 24 kd protein which may then serve as animal models for HCV infection.

It will be understood that the invention is described above by way of example and modifications within the scope and spirit of the invention may be made without the need for undue experiment or the exercise of inventive ingenuity.

References

1. European patent application EP-A-0318216

2. European patent application EP-A-0388232

3. Choo et al PNAS USA (1991) 88 2451–2455

4. Chien, D. Y. et al PNAS USA (1992) 89 10011–10015

5. Spaete, R. R. et al Virology (1992) 188 819–830

6. Gething et al Nature [needs complete reference]

7. "Flow Cytometry" in Methods of Cell Biology, 1990 Vol. 33 Academic Press San Diego 8. MorreD. J. et al., Methods Enzymol. (1994) 228, 448–450.

9. Laemmli et al Nature (1970) 27 680

What is claimed is:

1. A composition comprising a fragment of an unglycosylated, transmembrane protein wherein said unglycosylated, transmembrane protein has a molecular weight of about 24 kd as determined by SDS-PAGE, wherein said protein is stable to acetone precipitation, and further wherein said fragment is a truncated form of the protein that lacks a functional portion of a transmembrane domain and specifically binds the E2 protein of hepatitis C virus.

2. The composition of claim 1, wherein the protein is produced by a method comprising:

(a) providing a mammalian cell that expresses said 24 kd protein;

(b) recovering and solubilizing membranes from said mammalian cell to provide a cell membrane preparation;

(c) subjecting the cell membrane preparation to ammonium sulfate precipitation at less than 33% saturation and retaining the supernatant;

(d) subjecting the supernatant to ammonium sulfate precipitation at between 33% and 50% saturation and retaining the precipitate;

(e) resuspending the precipitate; and (f) subjecting the precipitate to hydrophobic interaction chromatography and recovering the nonretained material; and (g) cleaving a functional portion of a transmembrane domain out of the recovered material.

3. The composition of claim 2, wherein the mammalian cell that expresses said 24 kd protein hyperexpresses said 24 kd protein.

4. The composition of claim 3, wherein the mammalian cell is a MOLT-4 cell.

5. The composition of claim 4, wherein the cell membrane preparation is a plasma cell membrane preparation.

6. A fragment of an unglycosylated, transmembrane protein wherein said unglycosylated, transmembrane protein has a molecular weight of about 24 kd as determined by SDS-PAGE, wherein said protein is stable to acetone precipitation, and further wherein said fragment is a truncated form of the protein that lacks a functional portion of a transmembrane domain and specifically binds the E2 protein of hepatitis C virus.

7. The fragment of claim 6, wherein the fragment is produced by a method comprising:

(a) providing a mammalian cell that expresses said 24 kd protein;

(b) recovering and solubilizing membranes from said mammalian cell to provide a cell membrane preparation;

(c) subjecting the cell membrane preparation to ammonium sulfate precipitation at less than 33% saturation and retaining the supernatant;

(d) subjecting the supernatant to ammonium sulfate precipitation at between 33% and 50% saturation and retaining the precipitate;

(e) resuspending the precipitate; and (f) subjecting the precipitate to hydrophobic interaction chromatography and recovering the nonretained material; and (g) cleaving a functional portion of a transmembrane domain out of the recovered material.

8. The fragment of claim 7, wherein the mammalian cell that expresses said 24 kd protein hyperexpresses said 24 kd protein.

9. The fragment of claim 8, wherein the mammalian cell is a MOLT-4 cell.

10. The fragment of claim 7, wherein the cell membrane preparation is a plasma cell membrane preparation.

* * * * *